(12) United States Patent
Matsuoka et al.

(10) Patent No.: US 8,173,771 B2
(45) Date of Patent: May 8, 2012

(54) HUMANIN RECEPTOR OR HUMANIN-LIKE POLYPEPTIDE RECEPTOR

(75) Inventors: Masaaki Matsuoka, Tokyo (JP); Ikuo Nishimoto, Tokyo (JP); Tomo Nishimoto, legal representative, Ichikawa (JP); Sadakazu Aiso, Tokyo (JP)

(73) Assignee: Keio Univeristy, Tokyo (JP)

( * ) Notice: Subject to any disclaimer, the term of this patent is extended or adjusted under 35 U.S.C. 154(b) by 570 days.

(21) Appl. No.: 11/909,699

(22) PCT Filed: Apr. 10, 2006

(86) PCT No.: PCT/JP2006/307547
§ 371 (c)(1),
(2), (4) Date: Jul. 6, 2009

(87) PCT Pub. No.: WO2006/115026
PCT Pub. Date: Nov. 2, 2006

(65) Prior Publication Data
US 2010/0223684 A1 Sep. 2, 2010

(30) Foreign Application Priority Data

Apr. 22, 2005 (JP) ................................ 2005-124394
Sep. 5, 2005 (JP) ................................ 2005-255972

(51) Int. Cl.
*C07K 14/705* (2006.01)
(52) U.S. Cl. ....................................................... 530/350
(58) Field of Classification Search .................... None
See application file for complete search history.

(56) References Cited

FOREIGN PATENT DOCUMENTS

| EP | 1221480 A1 | 7/2002 |
|---|---|---|
| WO | 00/14204 A1 | 3/2000 |
| WO | 01/21787 A1 | 3/2001 |
| WO | 03/097687 A2 | 11/2003 |

OTHER PUBLICATIONS

Davis et al. LIFRbeta and gp130 as Heterodimerizing Signal Transducers of the Tripartite CNTF Receptor, Jun. 18, 1993, SCIENCE 160(5115):1805-1808.*
Hashimoto et al. Humanin Inhibits Neuronal Cell Death by Interacting with a Cytokine Receptor Complex or Complexes Involving CNTF Receptor alpha/WSX-1/gp130, Jun. 15, 2009, Molecular Biology of the Cell 20(12):2864-2873.*
Pflanzet al., WSX-1 and Glycoprotein 130 Constitute a Signal-Transducing Receptor for IL-27, Feb. 15, 2004, The Journal of Immunology 172(4):2225-2231.*
International Search Report, International Patent Application No. PCT/JP2006/307547, filed Apr. 10, 2006.
Pflanz, S., et al., "WSX-1 and Glycoprotein 130 Constitute a Signal-Transducing Receptor for IL-27," The Journal of Immunology, vol. 172, pp. 2225-2231, 2004.
Vollmer, P., et al., "A role for the immunoglobulin-like domain of the human IL-6 receptor, Intracellular protein transport and shedding," Eur. J. Biochem., vol. 263, pp. 438-446, 1999.
Hashimoto, Y., et al., "Involvement of tyrosine kinases and STAT3 in Humanin-mediated neuroprotection," Life Sciences, vol. 77, No. 24, pp. 3092-3104, 2005.
Fukada, Y., et al., "Two Signals Are Necessary for Cell Proliferation Induced by a Cytokine Receptor gp130: Involvement of STAT3 in Anti-Apoptosis," Immunity, vol. 5, pp. 449-460, 1996.
Artis, D., et al., "The IL-27 Receptor (WSX-1) is an Inhibitor of Innate and Adaptive Elements of Type 2 Immunity," The Journal of Immunology, vol. 173, pp. 5626-5634, 2004.
Benaki, D., et al., "Solution structure of humanin, a peptide against Alzheimer's disease-related neurotoxicity," Biochemical and biophysical Research Communications, vol. 329, pp. 152-160, 2005.
Boulay, J-L., et al., "Molecular Phylogeny within Type I Cytokines and Their Cognate Receptors," Immunity, vol. 19, pp. 159-163, 2003.
Boulanger, M.J., et al., "Shared Cytokine Signaling Receptors: Structural Insights from the Gp130 System," Advances in Protein Chemistry, vol. 68, pp. 107-146, 2004.
Chen, Q., et al., "Development of Th1-type immune responses requires the type I cytokine receptor TCCR," Nature, vol. 407, pp. 916-920, 2000.
Chow, D., et al., "A structural template for gp130-cytokine signaling assemblies," Biochimica et Biophysica Acta, vol. 1592, pp. 225-235, 2002.
Yoshida, H., et al., "WSX-1 Is Required for the Initiation of Th1 Responses and Resistance to L.. Major Infection," Immunity, vol. 15, pp. 569-578, 2001.
Fernandez-Madrid, I., et al., "Codon 618 Variant of Alzheimer Amyloid Gene Associated with Inherited Cerebral Hemorrhage," Annals of Neurology, vol. 30, No. 5, pp. 730-733, 1991.
Hardy, J., et al., "The Amyloid Hypothesis of Alzheimer's Disease: Progress and Problems on the Road to Therapeutics," Science, vol. 297, No. 5580, pp. 353-356, 2002.
Guo, B., et al., "Humanin peptide suppresses apoptosis by interfering with Bax activation," Nature, vol. 423, pp. 456-461, 2003.
Hashimoto, Y., et al., "Multiple Mechanisms Underlie Neurotoxicity by Different Types of Alzheimer's Disease Mutations of Amyloid Precursor Protein," Journal of Biological Chemistry, vol. 275, No. 44, pp. 34541-34551, 2000.
Hashimoto, Y., et al., "A rescue factor abolishing neuronal cell death by a wide spectrum of familial Alzheimer's disease genes and Aβ," Proceedings of the National Academy of Sciences of the U.S.A., vol. 98, No. 11, pp. 6336-6341, 2001.

(Continued)

*Primary Examiner* — John Ulm
(74) *Attorney, Agent, or Firm* — Ping Wang; Andrews Kurth, LLP

(57) ABSTRACT

One aspect of the present invention is directed to search receptors based on the information of HN signaling pathways in order to find Humanin receptor or Humanin-like polypeptide receptor (HNR), and to reveal a mechanism of promoting or suppressing the intracellular signal transduction for neuroprotecting activity of HN and identify a compound involved in the mechanism. The aspect of the invention is directed to a method for screening of HNR agonist and HNR antagonist, to utilize the screened compound in development of a drug for the treatment of neurodegenerative disease, and to provide an assay system of AD neuronal cell death, and to provide methods for the compulsory expression of HNR gene or knocking-out of intracellular genes.

2 Claims, 12 Drawing Sheets

OTHER PUBLICATIONS

Hashimoto, Y., et al., "Detailed Characterization of Neuroprotection by a Rescue Factor Humanin against Various Alzheimer's Disease-Relevant Insults," Journal of Neuroscience, vol. 21, No. 23, pp. 9235-9245, 2001.

Hashimoto, Y., et al., "Neurotoxic mechanisms triggered by Alzheimer's disease-linked mutant M146L presenilin 1: involvement of NO synthase via a novel pertussis toxin target," Journal of Neurochemistry, vol. 80, No. 3, pp. 246-237, 2002.

Hashimoto, Y., et al., "The Cytoplasmic Domain of Alzheimer's Amyloid-β Protein Precursor Causes Sustained Apoptosis Signal-Regulating Kinase 1/c-Jun NH2-Terminal Kinase-Mediated Neurotoxic Signal via Dimerization," Journal of Pharmacology and Experimental Therapeutics, vol. 306, No. 3, pp. 889-902, 2003.

Hashimoto, Y., et al., "Humanin antagonists: mutants that interfere with dimerization inhibit neuroprotection by Humanin," European Journal of Neuroscience, vol. 19, pp. 2357-2364, 2004.

Ip, N.Y., et al., "The Neurotrophins and CNTF: Two Families of Collaborative Neurotrophic Factors," Annu. Rev. Neurosci., vol. 19, pp. 491-515, 1996.

Jung, S.S., et al., "Humanin rescues human cerebrovascular smooth muscle cells from Aβ-induced toxicity," Journal of Neurochemistry, vol. 84, pp. 255-272, 2003.

Kanekura, K., et al., "Alsin, the Product of ALS2 Gene, Suppresses SOD1 Mutant Neurotoxicity through RhoGEF Domain by Interacting with SOD1 Mutants," The Journal of Biological Chemistry, vol. 279, No. 18, pp. 19247-19256, 2004.

Kang, J., et al., "The precursor of Alzheimer's disease amyloid A4 protein resembles a cell-surface receptor," Nature, vol. 325, pp. 733-736, 1987.

Kariya, S., et al., "Humanin inhibits cell death of serum-deprived PC12h cells," Neurochemistry, vol. 13, No. 6, pp. 903-907, 2002.

Kariya, S., et al., "Humanin improves impaired metabolic activity and prolongs survival of serum-deprived human lymphocytes," Molecular and Cellular Biochemistry, vol. 254, pp. 83-89, 2003.

Kawasumi, M., et al., "Targeted introduction of V642I mutation in amyloid precursor protein gene causes functional abnormality resembling early stage of Alzheimer's disease in aged mice," European Journal of Neuroscience, vol. 19, pp. 2826-2838, 2004.

Kumanogoh, A., et al., "Impairment of antigen-specific antibody productin in transgenic mice expressing a dominant-negative form of gp130," Proceedings of the National Academy of Sciences of the U.S.A., vol. 94, pp. 2478-2482, 1997.

Le, Y., et al., "Amyloid β42 Activates a G-Protein-Coupled Chemoattractant Receptor, FPR-Like-1," The Journal of Neuroscience, vol. 21, pp. 1-5, 2001.

Loo, D.T., et al., "Apoptosis is induced by β-amyloid in cultured central nervous system neurons," Proceedings of the National Academy of Sciences of the U.S.A., vol. 90, pp. 7951-7955, 1993.

Luo, J-J., et al., "Death of PC12 Cells and Hippocampal Neurons Induced by Adenoviral-Mediated FAD Human Amyloid Precursor Protein Gene Expression," Journal of Neuroscience Research, vol. 55, pp. 629-642, 1999.

Müller-Newen, G., et al., "Soluble IL-6 Receptor Potentiates the Antagonistic Activity of Soluble gp130 on IL-6 Responses," J. Immunol., vol. 161, pp. 6347-6355, 1998.

Minami, M., et al., "STAT3 activation is a critical step in gp130-mediated terminal differentiation and growth arrest of a myeloid cell line," Proeedings of the National Academy of Sciences, U.S.A., vol. 93, pp. 3963-3966, 1996.

Monsonego, A., et al., "Immunotherapeutic Approaches to Alzheimer's Disease," Science, vol. 302, No. 5646, pp. 834-838, 2003.

Neve, R.L., et al., "Alzheimer's disease: a dysfunction of the amyloid precursor protein," Brain Research, vol. 886, pp. 54-66, 2000.

Niikura, T., et al., "Characterization of V642I-AβPP-Induced Cytotoxicity in Primary Neurons," Journal of Neuroscience Research, vol. 77, pp. 54-62, 2004.

Nishimoto, I., et al., "Alzheimer amyloid protein precursor complexes with brain GTP-binding protein Go," Nature, vol. 362, pp. 75-79, 1993.

Nishimoto, I., et al., "Unravelling the role of Humanin," Trends in Molecular Medicine, vol. 10, No. 3, pp. 102-105, 2004.

Nishimura, I., et al., "Degeneration In Vivo of Rat Hippocampal Neurons by Wild-Type alzheimer Amyloid Precursor Protein Overexpressed by Adenovirus-Mediated Gene Transfer," Journal of Neuroscience, vol. 18, No. 7, pp. 2387-2398, 1999.

Pelletier, S., et al., "Rho Family GTPases Are Required for Activation of Jak/STAT Signaling by G Protein-Coupled Receptors," Molecular and Cellular Biology, vol. 23, No. 4, pp. 1316-1333, 2003.

Pflanz, S., et al., "IL-27, a Heterodimeric Cytokine Composed of EBI3 and p28 Protein, Induces Proliferation of Naive CD4+ T Cells," Immunity, vol. 16, pp. 779-790, 2002.

Rawlings, J.S., et al., "The Jak/STAT signaling pathway," Journal of Cellular Science, vol. 117, Pt. 8, pp. 1281-1283, 2004.

Rohn, T.T., et al., "A Monoclonal Antibody to Amyloid Precursor Protein Induces Neuronal Apoptosis," Journal of Neurochemistry, vol. 74, No. 6, pp. 2331-2342, 2000.

Salcedo, R., et al., "IL-27 Mediates Complete Regression of Orthotopic Primary and Metastatic Murine Neuroblastoma Tumors: Role for CD8+ T Cells," Journal of Immunology, vol. 173, pp. 7170-7182, 2004.

Scheller, J., et al., "No inhibition of IL-27 signaling by soluble gp130," Biochemical and Biophysical Research Communications, vol. 326, pp. 724-728, 2005.

Shastry, B.S., et al., "Genes and susceptible loci of Alzheimer's disease," Brain Research Bulletin, vol. 48, No. 2, pp. 121-127, 1999.

Sponne, I., et al., "Humanin rescues cortical neurons from prion-peptide-induced apoptosis," Molecular and Cellular Neuroscience, vol. 25, No. 1, pp. 95-102, 2004.

Sprecher, C.A., et al., "Cloning and Characterization of a Novel Class I Cytokine Receptor," Biochem. Biophys. Res. Commun., vol. 246, pp. 82-90, 1998.

Sudo, H., et al., "Secreted Aβ Does Not Mediate Neurotoxicity by Antibody-Stimulated Amyloid Precursor Protein" Biochemical and Biophysical Research Communications, vol. 282, pp. 548-556, 2001.

Sui, G., et al., "A DNA vector-based RNAi technology to suppress gene expression in mammalian cells," Proceedings of the National Academy of Sciences, U.S.A., vol. 99, pp. 5515-5520, 2002.

Tajima, H., et al., "A Humanin Derivative, S14G-HN, Prevents Amyloid-β-Induced Memory Impairment in Mice," Journal of Neuroscience Research, vol. 79, pp. 714-723, 2005.

Terashita, K., et al., "Two serine residues distinctly regulate the rescue function of Humanin, an inhibiting factor of Alzheimer's disease-related neurotoxicity: functional potentiation by isomerization and dimerization," Journal of Neurochemistry, vol. 85, pp. 1521-1538, 2003.

Taga, T., et al., "gp130 and the Interleukin-6 Family of Cytokines," Annual Review of Immunology, vol. 15, pp. 797-819, 1997.

Tsukamoto, E., et al., "Characterization of the Toxic Mechanism Triggered by Alzheimer's Amyloid-β Peptides Via p75 Neurotrophin Receptor in Neuronal Hybrid Cells," Journal of Neuroscience Research, vol. 73, pp. 627-636, 2003.

Turkson, J., et al., "STAT proteins: novel molecular targets for cancer drug discovery," Oncogene, vol. 19, No. 56, pp. 6613-6626, 2000.

Wolozin, B., et al., "Participation of Presenilin 2 in Apoptosis: Enhanced Basal Activity Conferred vy an Alzheimer Mutation," Science, vol. 274, pp. 1710-1713, 1996.

Yamagishi, Y., et al., "Identification of essential amino acides in Humanin, a neuroprotective factor against Alzheimer's disease-relevant insults," Peptides, vol. 24, pp. 585-595, 2003.

Yamatsuji, T., et al., "G Protein-Mediated Neuronal DNA Fragmentation Induced by Familial Alzheimer's Disease-Associated Mutants of APP," Science, vol. 272, pp. 1349-1352, 1996.

Yamatsuji, T., et al., "Expression of V642 APP mutant causes cellular apoptosis as Alzheimer trait-linked phenotype," EMBO Journal, vol. 15, No. 3, pp. 498-509, 1996.

Ying, G., et al., "Humanin, a Newly Identified Neuroprotective Factor, Uses the G Protein-Coupled Formylpeptide Receptor-Like-1 as a Functional Receptor," Journal of Immunology, vol. 172, No. 11, pp. 7078-7085, 2004.

Villarino, A.V., et al., "Understanding the Pro- and Anti-Inflammatory Properties of IL-27," Journal of Immunology, vol. 173, pp. 715-720, 2004.

David Man, "Solution Structure of the C-terminal Domain of the Ciliary Neurotrophic Factor (CNTF) Receptor and Ligand Free Associations among Components of the CNTF Receptor Complex", XP-002508982, The Journal of Biological Chemistry, 2003, pp. 23285-23294, vol. 278, No. 26, Issue of Jun. 27, The American Society for Biochemistry and Molecular Biology, Inc.

Stefan Pflanz, et al., "WSX-1 and Glycoprotein 130 Constitute a Signal-Transducing Receptor for IL-27", XP003006431, The Journal of Immunology, 2004, pp. 2225-2231,172, The American Association of Immunologists, Inc.

Masataka Harada, et al., "N-Formylated humanin activates both formyl peptide receptor-like 1 and 2", Biochemical and Biophysical Research Communications, 2004, pp. 255-261,324, Elsevier Inc.

Nancy Y. Ip, et al., "CNTF and LIF Act on Neuronal Cells via Shared Signaling Pathways that Involve the IL-6 Signal Transducing Receptor Component gp130", XP002956083, Cell, 1992, pp. 1121-1132, vol. 69, Cell Press.

Takayoshi Mamiya, et al., "[Gly14]-Humanin improved the learning and memory impairment induced by scopolamine in vivo", XP001153677, British Journal of Pharmacology, 2001, pp. 1597-1599, 134, Nature Publishing Group.

ALS CNTF Treatment Study Group, "A double-blind placebo-controlled clinical trial of subcutaneous recombinant human ciliary neurotrophic factor (rHCNTF) in amyotrophic lateral sclerosis", XP000971863, Molecular and Cellular Neuroscience, 1996, pp. 1244-1249, The American Academy of Neurology.

Takako Niikura, et al., "Death and Survival of Neuronal Cells Exposed to Alzheimer's Insults", XP002508983, Journal of Neuroscience Research, 2002, pp. 380-391, 70, Wiley-Liss Inc.

\* cited by examiner

Figure 2
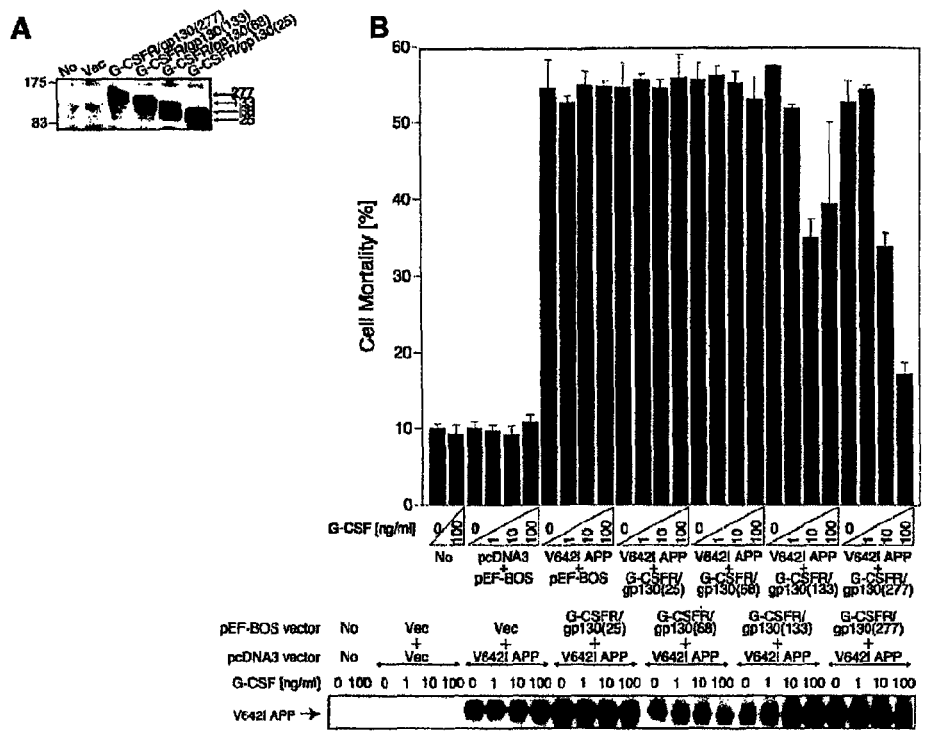
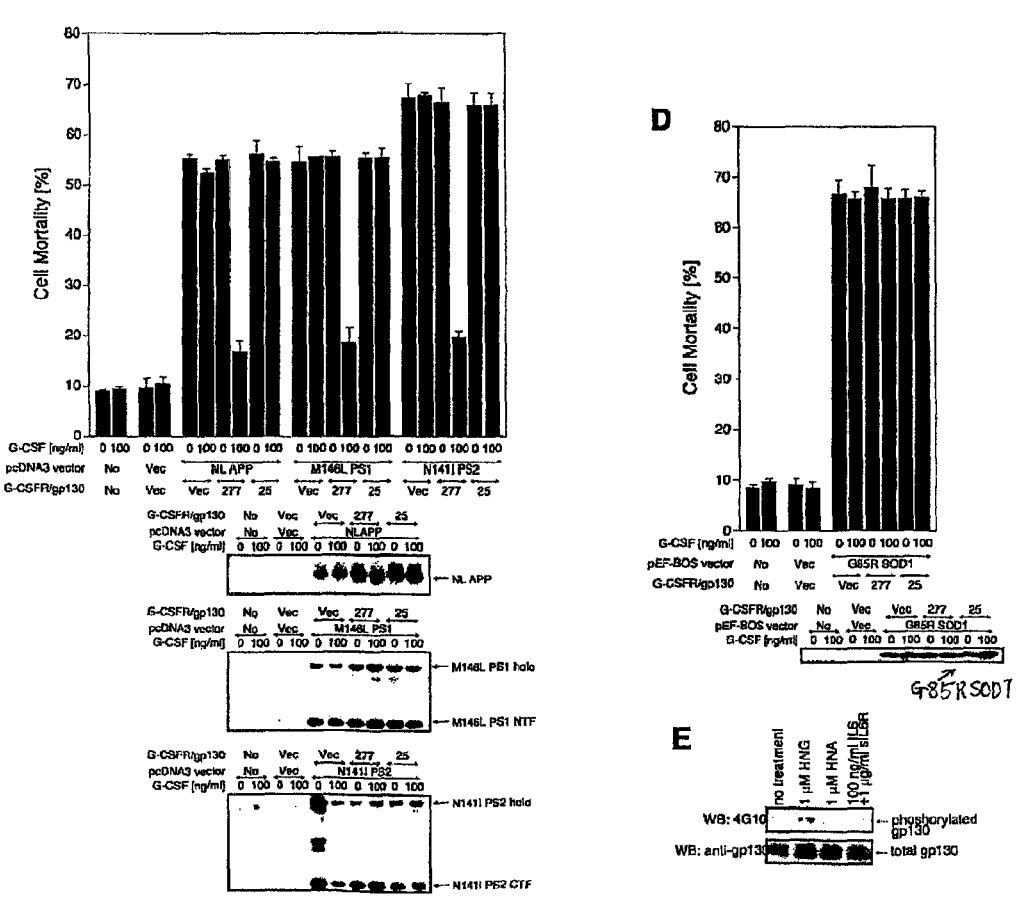

Figure 9
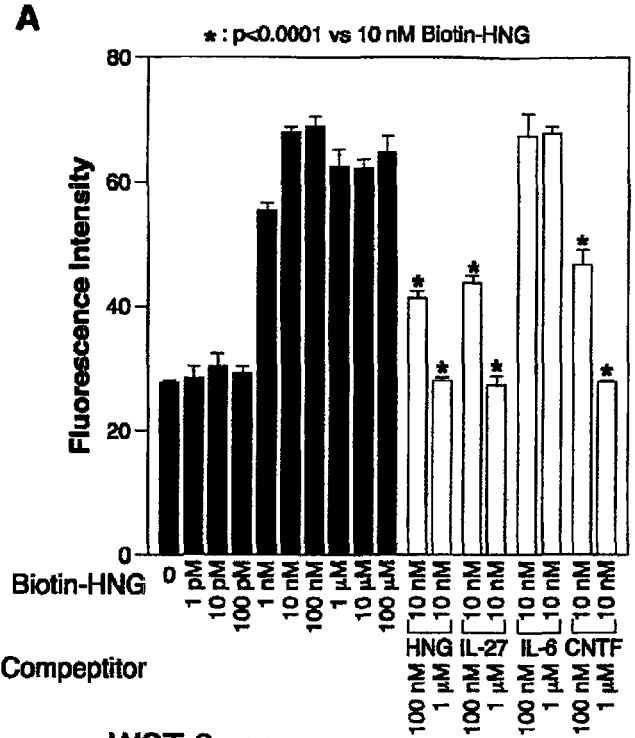
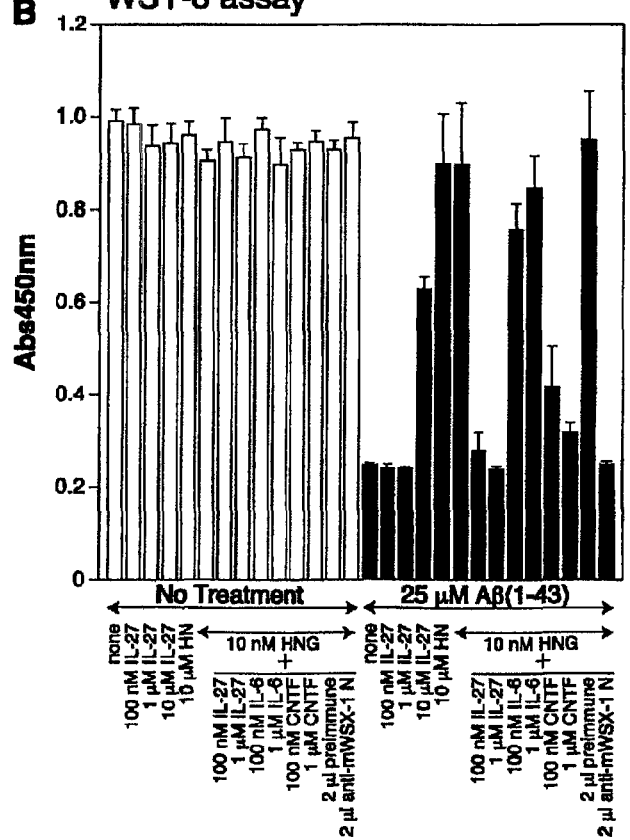

HUMANIN RECEPTOR OR HUMANIN-LIKE POLYPEPTIDE RECEPTOR

FIELD

The invention relates to a Humanin receptor or Humanin-like polypeptide receptor (both of which may be also referred to hereinafter as "HNR"), to a transformant cell compulsorily expressing the receptor, to a method for screening a compound that binds to the receptor, to a pharmaceutical composition comprising the compounds and the like.

BACKGROUND

Neuronal loss, which has been considered to be directly linked to the major neurological manifestations of Alzheimer's disease (AD), is an important target for AD therapy although the pathological mechanism leading to neuronal loss still remains unknown. In vitro, a variety of AD-related insults, such as overexpression of FAD-related mutants and increased levels of toxic amyloid b peptides (Aβs) derived from Amyloid-β precursor protein (APP), induce neuronal cell death via multiple death pathways.

Familial AD (FAD) has been identified to be caused by missense mutations in three genes: APP, presenilin-1 (PS1), and presenilin-2 (PS2) [Shastry and Giblin, 1999]. Although it remains unknown how these mutant genes contribute to neuronal loss in FAD brain in vivo, multiple groups have provided evidence that expression of the FAD-associated mutant APP and PS genes causes neuronal cell death in cultured cells (Yamatsuji et al., 1996a, b; Wolozin et al., 1996; Zhao et al., 1997; Nishimura et al, 1998; Luo et al., 1999; Hashimoto et al., 2000) and primary cortical neurons (Niikura et al., 2004).

In addition, increased levels of toxic Aβs, which are considered to be closely linked to AD pathogenesis (Hardy and Selkoe, 2002), result in neuronal cell death in vitro although superphysiological concentrations of Aβ are required (Loo et al., 1994; Hashimoto et al., 2001; Hashimoto et al., 2004).

By performing a 'death-trap' screening, an unbiased functional screening of molecules that allows dying cells to survive, with a cDNA library constructed from an occipital lobe of the brain of an autopsy-diagnosed AD patient, we identified a cDNA encoding the 24 amino acids peptide MAPRGFSCLLLLTSEIDLPVKRRA (SEQ ID NO:1) named Humanin (HN) (WO01/021787) Polypeptide inhibiting neuronal cell death, Humanin), which suppresses neuronal cell death by all AD-related insults such as various FAD genes, anti-APP antibody, and neurotoxic Aβ peptides (Hashimoto et al., 2001a and b; Nishimura et al., 2004). Ten mM of HN completely inhibits neurotoxicity induced by various AD-related insults. It has also been shown in follow-up studies that HN is also effective in inhibiting certain types of neuronal and non-neuronal cell death, such as serum-deprivation-induced cell death of PC12h cells (Kariya et al., 2002) and lymphocytes (Kariya et al., 2003), Aβ toxicity in human cerebrovascular smooth muscle cells (Jung et al, 2003), and prion-derived peptide-induced neurotoxicity (Sponne et al., 2004).

We have shown that HN is secreted from cells and inhibits neuronal cell death by AD-related insults from outside of cells via its putative receptor on the membrane (Hashimoto et al., 2001a; Nishimura et al., 2004).

Most recently, Ying et al. (2004) have reported that HN inhibits Aβ (1-42)-induced neurotoxicity by binding to pertussis toxin (PTX)-sensitive G protein-coupled human formylpeptide receptor-like-1 (FPRL-1) as a HN receptor using PC12 neuroblastoma cells. They suggested that HN blocks Aβ-induced neurotoxicity by competing with Aβ for FPRL-1. However, after we have studied how FPRL-1 is involved in HN-mediated protection against AD-related neuronal insults, we found that FPRL-1 is not involved in HN-mediated neuroprotection in F11 neurohybrid cells or primary cortical neurons (Hashimoto et al., 2005), indicating that there are other receptors than FPRL-1, which may mediate HN-induced neuroprotection.

In addition, we revealed that STAT3 as well as a certain kind of tyrosine kinase are involved in HN-mediated neuroprotection (Hashimoto et al. 2005), suggesting that some cytokine receptor-like receptors are involved in their signaling pathway.

gp130 is a component of cytokine receptor common to interleukin-6 (IL-6) receptor family members. gp130-containing receptors are stimulated by several type I cytokines consisting of IL-6, IL-11, Leukemia-inhibitory factor (LIF), ciliary neurotrophic factor (CNTF), OncostatinM (OSM), and Cardiotropin-1. Binding of these cytokines to the above cognate receptors leads to homodimerization of gp130, or to heterodimerization between gp130 and a gp130-related receptor such as the LIF receptor, the OSM receptor or WSX-1 (IL-27 receptor), eventually transmitting cytokine signals to intracellular signal cascades mediated by both JAK/STAT and RAS/MAPK signaling pathways (Taga et al., 1997; Boulay et al., 2003; Boulanger et al., 2004). Most recently, it has been shown that IL-27 (IL-27p28/EBV-induced gene 3), which belongs to IL-6/IL-12 family cytokines, modifies Th-1 and Th-2 immunological response (Yoshida et al., 2004) by binding to WSX-1/gp130 (Plan et al, 2004). CNTF receptor alpha chain (CNTR-R) is a gp130-related receptor, which does not have an intracellular signaling domain. WO01/021787 and WO03/097687.

PROBLEMS TO BE SOLVED

The purpose of this invention is therefore to search receptors based on the information about HN signaling pathway in order to finally find Humanin receptor or Humanin-like polypeptide receptor (HNR), and to reveal a mechanism of promoting or suppressing the intracellular signal transduction for showing neuroprotecting activity of HN and identify a compound involved in the mechanism, to establish a method for screening of HNR agonist and HNR antagonist, to utilize the screened compound in development of a drug for the treatment of neurodegenerative disease, especially AD, to provide an assay system of AD neuronal cell death, and to provide methods for the compulsory expression of HNR gene or knocking-out of intracellular genes.

SUMMARY

The present invention relates to the following aspects.

A Humanin receptor or Humanin-like polypeptide receptor (HNR) comprising at least two kinds of proteins selected from the group consisting of gp130 or its partial polypeptide, CNTF receptor a chain (CNTF-R) and WSX-1.

A Humanin receptor or Humanin-like polypeptide receptor (HNR) consisting of gp130 or its partial polypeptide, CNTF-R and WSX-1.

A Humanin receptor or Humanin-like polypeptide receptor (HNR) consisting of gp130 or its partial polypeptide and WSX-1.

A Humanin receptor or Humanin-like polypeptide receptor (HNR) of Claim 1, wherein the gp130 partial polypeptide comprises at least an amino acid sequence of amino acids 1-133 residues in an intracellular domain.

A Humanin receptor or Humanin-like polypeptide receptor (HNR) consisting of CNTF-R and WSX-1.

A Humanin receptor or Humanin-like polypeptide receptor (HNR) of Claim 1, wherein gp130, CNTF-R and WSX-1 are a protein derived from human.

A method for screening of a compound that binds to Humanin receptor or Humanin-like polypeptide receptor (HNR) of Claim 1.

A screening method of Claim 7, wherein the compound that binds to Humanin receptor or Humanin-like polypeptide receptor (HNR) binds to an extracellular domain of the receptor.

A screening method of Claim 7, wherein the compound that binds to Humanin receptor or Humanin-like polypeptide receptor (HNR) is an agonist for the receptor.

A screening method of Claim 7, comprising the steps:
(a) a step of placing a subject sample in contact with Humanin receptor or Humanin-like polypeptide receptor (HNR) or at least one protein that constitutes it;
(b) a step of determining a binding characteristics between the receptor and the compound comprised in the subject sample; and
(c) a step of selecting the compound that binds to the receptor.

A screening method of Claim 12, wherein a subject sample is placed in contact with Humanin receptor or Humanin-like polypeptide receptor (HNR) or at least one protein that constitutes it in the presence of Humanin or Humanin-like polypeptide.

A screening method of Claim 12, wherein Humanin receptor or Humanin-like polypeptide receptor (HNR) or at least one protein that constitutes it is compulsorily expressed in a cell.

A screening method of Claim 12, wherein Humanin receptor or Humanin-like polypeptide receptor (HNR) is compulsorily expressed by a cell transformed with an expression vector comprising a gene encoding at least one protein that constitutes the receptor.

A screening method of Claim 12, wherein the binding characteristics between the receptor and the compound is determined by detecting a change in a suppressing or inhibiting function for neuronal cell death.

A screening method of claim 12, wherein the binding characteristics between the receptor and the compound is determined by detecting increase or decrease of phosphorylation of tyrosine 705 of STAT3.

A screening method of Claim 7, which is performed in a cell-free system.

A cell transformed with an expression vector comprising a gene encoding at least one protein that constitutes Humanin receptor or Humanin-like polypeptide receptor (HNR), which is selected from the group consisting of gp130, CNTF-R and WSX-1.

A transformed cell of Claim 19, wherein Humanin receptor or Humanin-like polypeptide receptor (HNR) is compulsorily expressed.

A cell in which a gene encoding at least one protein that constitutes Humanin receptor or Humanin-like polypeptide receptor (HNR), which is selected from the group consisting of gp130, CNTF-R and WSX-1, is knocked out.

A cell of Claim 21, which is an ES cell.

A knockout animal except human, which is derived from the cell of Claim 22.

A knockout animal of Claim 23, which is homozygous.

A knockout animal of Claim 23, which is a rodent.

A pharmaceutical composition as an inhibitor of neuronal cell death, comprising the compound that can bind to Humanin receptor or Humanin-like polypeptide receptor (HNR) of Claim 1 as an effective component.

A pharmaceutical composition for use of prevention or treatment of neurodegenerative diseases, comprising the compound that binds to Humanin receptor or Humanin-like polypeptide receptor (HNR) of Claim 1 as an effective component.

A pharmaceutical composition for use of prevention or treatment of Alzheimer's disease, comprising the compound that binds to Humanin receptor or Humanin-like polypeptide receptor (HNR) of Claim 1 as an effective component.

A pharmaceutical composition for use of prevention or treatment of amyotrophic lateral sclerosis, comprising the compound that binds to Humanin receptor or Humanin-like polypeptide receptor (HNR) of Claim 1 as an effective component.

A pharmaceutical composition for use of prevention or treatment of mad cow disease, comprising the compound that binds to Humanin receptor or Humanin-like polypeptide receptor (HNR) of Claim 1 as an effective component.

A pharmaceutical composition for use of prevention or treatment of vascular dementia, comprising the compound that binds to Humanin receptor or Humanin-like polypeptide receptor (HNR) of Claim 1 as an effective component.

An antibody that specifically binds to Humanin receptor or Humanin-like polypeptide receptor (HNR) of Claim 1.

The present invention has revealed the structure of Humanin receptor or Humanin-like polypeptide receptor (HNR), and made it possible to provide a method for screening a compound that can bind to the above receptor and a pharmaceutical composition comprising said compound and the like.

Figure 1:
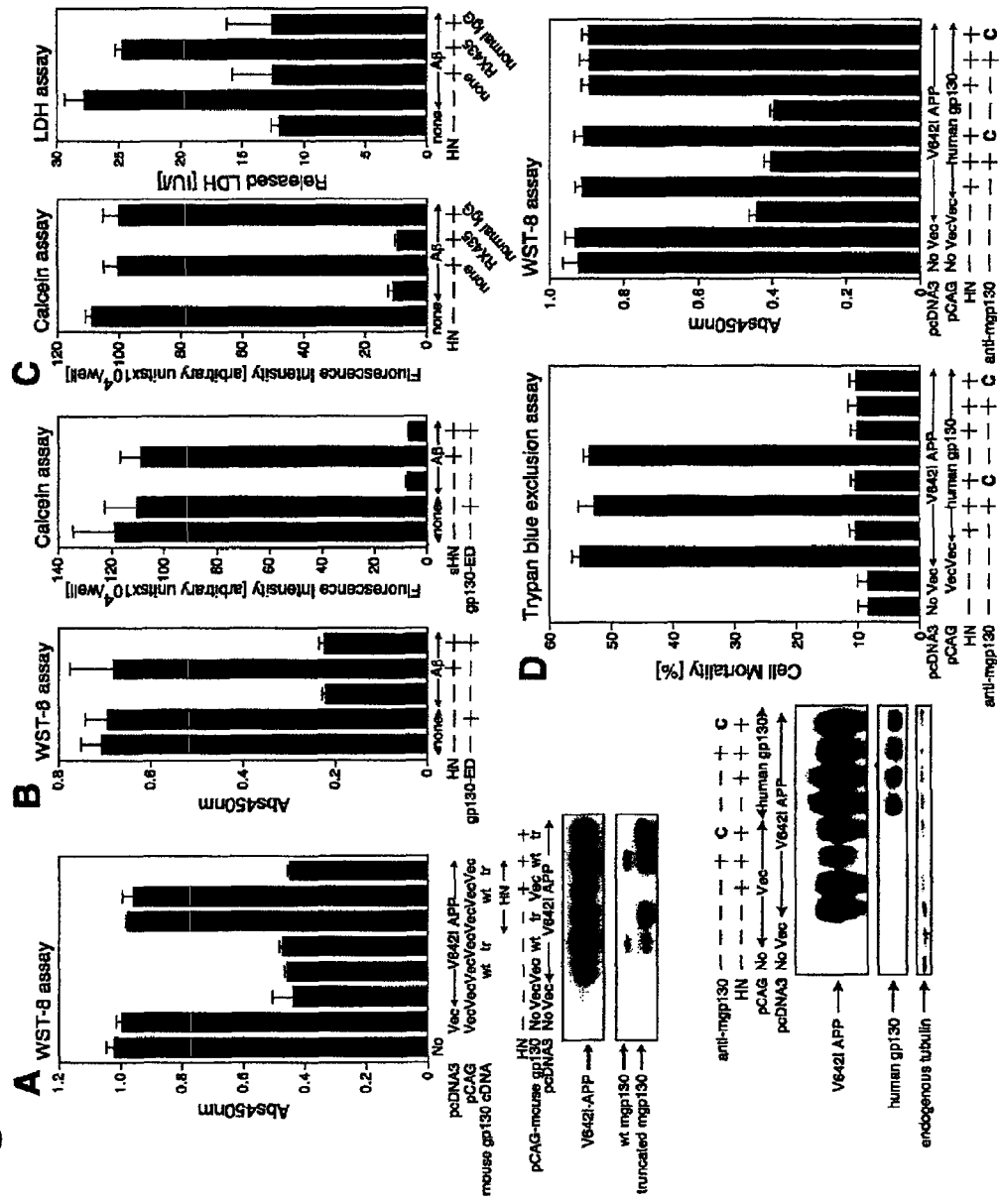
FIGS. 1 (A)-(D)

A) F11 cells were transfected with 0.5 μg of the pcDNA3 vector or pcDNA3-V642I-APP in association with 0.5 μg of the pCAG vector or pCAG-wild-type mouse gp130 (mgp130wt) or pCAG-mouse gp130 extracellular domain (mgp130tr). Cell viability was determined by WST-8 assay at 72 hr after the transfection. Below are shown the results of the expression of V642I-APP, and mgp130wt or mgp130tr, which were confirmed by immunoblot analysis (photos).

B) PCNs were incubated with 25 μM Aβ (upper) in the presence of 10 μg of recombinant soluble human gp130 (lower "+") or BSA (lower "−"). Cell viability was determined by WST-8 assay (upper) or Calcein fluorescence assay (lower) at 72 hr after the onset of treatment with Aβ.

C) PCNs were incubated with 25 μM Aβ (1-43) in the presence of 1 μg of neutralizing anti-mouse gp130 antibody (RX435) or control IgG. Cell viability and cell mortality were determined by Calcein fluorescence (left panel) and LDH assays (right panel), respectively, at 72 hr after the onset of treatment with Aβ (1-43).

D) F11 cells were transfected with 0.5 μg of the pcDNA3 vector or pcDNA3-V642I-APP in association with 0.5 μg of the pEFBos vector or pEFBos-wild-type human gp130 (gp130wt). At 24 hr after transfection, the cells were added with 1 μg of neutralizing anti-mouse gp130 antibody. Cell mortality (left panel) and cell viability (right panel) were determined by Trypan blue exclusion assay and WST-8 assay at 72 hr after transfection. Below are shown the results of the expression of V642I-APP, and human gp130wt, which were confirmed by immunoblot analysis (photos).

FIGS. 2 (A)-(E)

A) F11 cells were transfected with 0.5 μg of the pcDNA3 vector or pcDNA3-APP in association with 0.5 μg of the pEFBos vector or the pEFBos vector encoding the extracellular domain of the human G-CSF receptor fused to the full transmembrane domain and a C-terminally truncated intracytoplasmic (intracellular) domain of gp130 (named "G-CSFR/gp130"). The results of the expression of each chimeric proteins after 48 hours, which were confirmed by immunoblot analysis, were shown in photos.

B) F11 cells were transfected with 0.5 µg of the pcDNA3 vector or pcDNA3-APP in association with 0.5 µg of the pEFBos vector or the pEFBos vectors encoding the extracellular domain of the human G-CSF receptor fused to the full transmembrane domain and a C-terminally truncated intracytoplasmic domain of gp130 (named "G-CSFR/gp130"). G-CSFR/gp130 (277) contains the full intracytoplasmic domain of gp130 corresponding to amino acids 1-277, while G-CSFR/gp130 (25), (68), and (133) contain the intracytoplasmic domains corresponding to amino acids 1-25, 1-68, and 1-133, respectively. At 24 hr after transfection, the cells were added with indicated amounts of human G-CSF. Cell mortality was determined by Trypan blue exclusion assay at 72 hr after transfection. The results of immunoblot analysis of the expression of V6421-APP are shown in photos.

C) Instead of the pcDNA3-V6421-APP vector, pcDNA3-K595 N/M596L-APP (NL-APP), M146L-PS1 and N141-I-PS2 vectors were used to do the same experiments as in FIG. 2A. The results of immunoblot analysis of the expression of NL-APP, M146L-PS1 and N141-I-PS2 are shown in photos.

D) F11 cells were transfected with 0.5 µg of the pEFBos vector or pEF-G85R-SOD1 in association with 0.5 µg of the pEFBos vector or each pEFBos vector encoding G-CSFR/gp130 (277) or G-CSFR/gp130 (25). At 24 hr after transfection, the cells were added with indicated amounts of human G-CSF. Cell mortality was determined by Trypan blue exclusion assay at 72 hr after transfection. The results of the expression of G85R-SOD1, which were confirmed by the immunoblot analysis, are shown in photos.

E) Phosphorylation of tyrosine of gp130 was increased by HN treatment. PCNs (1.0×10⁶ cells/well in 6-well plated) (DIV3) was transfected with human gp130-encoding adenoviruses. After 60 hrs were added 1 µM HNG, 1 µM HNA, 100 ng/ml of rat IL-6 and 1 µg/ml of sIL-6R to the infected cells and incubated at 37 C.° for 15 min. The results of immunoblot of the precipitate immunoprecipitated with anti-gp130 antibody with a phosphotyrosine antibody are shown in photos.

FIGS. 3 (A)-(E)

A) PCNs, seeded at 2.5 or 5.0×10⁴/well in 96 dishes, were incubated with or without 25 µM of Aβ (1-43) and in the presence or the absence of indicated amounts of indicated cytokines. At 72 hr after incubation, the cells were harvested for WST-8 assays or/and Calcein fluorescence assays to show cell viability.

B) The soluble IL-6 receptor-α (sIL-6R) or the soluble CNTF-R (100 ng/ml) were added to the cells as in the above A), followed by the stimulation with its ligand, IL-6 or CNTF (100 ng/ml), respectively to show the effects on the neuronal cell death due to Aβ. The right and left graphs show the cell viabilities determined by WST-8 assays and Calcein fluorescence assays, respectively.

C) The neutralizing antibodies (1 µg) for the mouse gp130, mouse LIFR, mouse IL-11R and rat CNTF-R were added as in the above A), and cell viability was determined by Calcein fluorescence assays after 72 hours.

D) F11 cells were transfected with an indicated amount of pRNA-U6.1/Shuttle vector (empty), pRNA-U6.1/Shuttle-IL-6R siRNA, or pRNA-U6.1/Shuttle-LIFR siRNA. At 72 hrs after transfection, total RNA was extracted, and an amount of IL-6R mRNA and LIFR mRNA was quantatively measured by real-time PCR. The amount of G3PDH was also determined an internal control and used for calibration. The change of the proteins was determined by immunoblot analysis.

E) F11 cells were transfected with an indicated amount of pRNA-U6.1/Shuttle vector (empty), pRNA-U6.1/Shuttle-IL-6R siRNA, or pRNA-U6.1/Shuttle-LIFR siRNA. At 48 hrs after transfection, the cells were treated with 100 ng/ml IL-6, 100 ng/ml CNTF or 1 µM HNG at 37° for 15 min, and harvested. The results of immunoblot analysis using anti-phophoSTAT3 (Tyr$^{705}$) antibody and anti-STAT3 antibody were shown in photos.

FIGS. 4 (A)-(C)

A) F11 cells were transfected with 0.5 µg of the pEF/BOS vector, pEF-mycHis CREME9, pEF-mycHishuman WSX-1, or pEF-V5-human CNTF-R in association with 0.5 µg of pCAG-human gp130, or transfected with 0.5 µg of pEF-mycHis human WSX-1 and pEF-V5-human CNTF-R and pCAG-human gp130. To keep the total amounts of transfected vectors to be 1.5 µg, an appropriate amount of the pEFBOS vector was added. The graphs show the results of a binding amount of the biotin-labeled HN to each transfected cell by the detection of immunofluorescence reaction. The protein expression by immunoblot analysis is shown below in photos.

B) F11 cells were transfected with 0.5 µg of pEF-myc His human CREME9 or pEF-mycHis human WSX-1 in association with 0.5 µg of pCAG-human gp130. For competition, 10 µM of non-labeled (cold) HNG or HNA was added for some experiments. Fluorescence signals were detected with a laser-scanning, confocal microscope LSM (Carl Zeiss, Germany) (right panels).

C) The photos show the results of in vitro pull down assay using HN- or HNA-conjugated Sepharose 4B bead. WSX-1, CNTF-R, and IL-6 were over-expressed in F11 cells and the pull down assay was made using the above 4B bead. Immunoblot analysis was done using PO4 antibody against Humanin (lower panes). HN or HNA comprised in the above Sepharose 4B bead was compared with synthesized HN peptide (50 pmol) as a positive control.

FIGS. 5 (A)-(C)

The graphs show the results obtained by knock-down of the expression of CNTF-R or WSX-1 in F11 cells by means of plasmid siRNA method, in order to confirm that these proteins are involved in the HN-mediated signaling of neuroprotecting function.

A) F11 cells were transfected with indicated amounts of pRNA-U6.1/Shuttle vector (NO), pRNA-U6.1/Shuttle-siWSX-1 (W), or pRNA-U6.1/Shuttle-siCNTF-R (C). Seventy-two hrs after transfection, the cells were lysed for RNA extraction. The amounts of mRNA were determined by real-time PCR and the amounts of protein were determined by immunoblot analysis.

B) F11 cells were transfected with 0.5 µg of the pcDNA3 vector or pcDNA3-V642I-APP in association with pRNA-U6.1/Shuttle vector (NO), pRNA-U6.1/Shuttle-siWSX-1 (W), pRNA-U6.1/Shuttle-siCNTF-R (C), or pRNA-U6.1/Shuttle-siFPR-2 (F) (Hashimoto et al. 2005). At 24 hrs after transfection, the cells were added with or without 10 nM of HNG. At 72 hrs after transfection, the cells were harvested for WST-8 assays.

C) F11 cells were transfected with 0.5 µg of the pcDNA3 vector or pcDNA3-V642I-APP in association with pRNA-U6.1/Shuttle vector (Vec), pRNA-U6.1/Shuttle-siWSX-1 (W), or pRNA-U6.1/Shuttle-siCNTF-R (C) together with 1 µg of the pEFBos vector, pEF-mycHis-human WSX-1, or pEF-V5-human CNTF-R. At 24 hrs after transfection, the cells were added with or without 10 nM of HNG. At 72 hrs after transfection, the cells were harvested for WST-8 assays.

FIGS. 6 (A)-(B)

A) COS7 cells were transfected with 0.5 μg of the pEFBos vector, pEF-mycHis-human WSX-1, or/and pEF-V5-human CNTF-R. The total amounts of transfected vectors were 1.0 μg. 72 hrs after transfection, the cells were harvested for immunoprecipitation with antibodies against myc (for myc-WSX-1) or anti-hCNTF-R antibody. Resultant precipitates were subject to immunoblot analysis with a mixture of antibodies against myc and V5. The results are shown in photos.

B) F11 cells were treated with 10 μM HNA or 10 nM HNG for 1, 3 and 6 hrs. The cells were treated with 1 mM BS3, as a cross-linker at 30 min before harvesting. The cells were harvested for immunoprecipitation with antibodies against gp130 or CNTF-R. Resultant precipitates were subject to immunoblot analysis with antibodies against WSX-1, gp103 and CNTF-R. A control immunoprecipitation was done using an antibody against SOD1. Input amounts of lysates were one twentieth the amount used for immunoprecipitation.

FIG. 7

F11 cells were transfected with pcDNA3 vector or pcDNA3-V642I-APP. At 10 hrs after transfection, the cells were added with 10 nM of HNG, 10 μM of HN or an indicated amount of human IL-27. In some experiments, the indicated amount of IL-27 or IL-6 was simultaneously administered with HNG. At 72 hrs after administration, WST-8 assay was carried out. The expression of V642I-APP was checked as well with respect to the cells allotted with numbers. The expression of V642I-APP determined by immunoblot analysis was shown below in a photo.

FIGS. 8 (A)-(B)

A) F11 cells were seeded on 96-well plates coated with poly-L-lysine ($7 \times 10^3$ cells/well). An indicated amount of biotin-HN or biotin-HNG was added to the cells with or without 10 μM of unlabelled HNG or HNA, followed by a binding assay based on immunofluorescence reaction (2) (left panels). On the other hand, F11 cells were transfected with 0.5 μg of pcDNA3.1/GS-human CNTF-R, pEF1/MycHis-human WSX-1, and 1.0 μg of pCAG-human gp130. At 24 hrs after the transfection, the cells were re-seeded on 96-well plates coated with poly-L-lysine ($7 \times 10^3$ cells/well). After 36 hrs the re-seeding, an indicated amount of biotin-HN or biotin-HNG was added to the cells with or without 10 μM of unlabeled HNG or HNA, followed by a binding assay based on immunofluorescence reaction (2) (right panels).

B) F11 cells were transfected with 0.5 μg of pRNA-U1.6/Shuttle vector, pRNA-U6.1/Shuttle-WSX-1 siRNA, pRNA-U6.1/Shuttle-CNTF-R siRNA, both pRNA-U6.1/Shuttle-WSX-1 siRNA and pRNA-U6.1/Shuttle-CNTF-R siRNA (0.5 μg each), pRNA-U6.1/Shuttle-FPR2 siRNA or pRNA-U6.1/Shuttle-LIFR siRNA. The total amount of vectors was adjusted to be 1.0 μg by including a backbone vector. At 24 hrs after the transfection, an indicated amount of biotin-HNG was added with or without unlabeled HNG, followed by a binding assay based on immunofluorescence reaction (2) at 72 hrs after the transfection.

FIGS. 9 (A)-(B)

A) An indicated amount of biotin-HNG, biotin-HN or human IL-27 was added to PCN cells that had been treated for three days on 96-well plate coated with poly-L-lysine ($7 \times 10^4$ cells/well), followed by a binding assay based on immunofluorescence reaction (2). In some experiments, an indicated amount of unlabeled IL-27, CNTF, IL-6 or HNG was added simultaneously in addition to 10 nM of biotin-HNG.

B) An indicated amount of human IL-27, both 10 nM of HNG and an indicated amount of IL-27, IL-6, CNTF, or 2 μL of an anti-mWSX-1-N antibody or preimmune sera was added to PCN cells that had been treated for three days on 96-well plate coated with poly-L-lysine ($5 \times 10^4$ cells/well), followed by the treatment with 10 μM of Aβ (1-43) at 16 hrs after the addition. WST-8 assay was performed at 72 hrs after the treatment.

FIGS. 10 (A)-(B)

A) Immunoblot analysis was performed with the extract of F11 cells (lane 1). At the same time, immunoprecipitation was performed with the anti-mWSX-1-C antibody using ten times the amount of said extract (lane 3) or with preimmune serum as a negative control in a quasi-immunoprecipitation (lane 2).

B) Immunoblot analysis was performed with the anti-mWSX-1-C antibody using the extract of PCNs (DIV3) or F11 cells. The results were shown in photos.

FIGS. 11 (A)-(B)

A) F11 cells were added with an indicated amount of HN, HNG or HNA and harvested 15 min later for immunoblot analysis with antibodies recognizing phosphotyrosine 705 of STAT3 or STAT3. The results are shown in photos.

B) F11 cells were transfected with 0.5 μg of pRNA-U1.6/Shuttle vector, pRNA-U6.1/Shuttle-WSX-1 siRNA, pRNA-U6.1/Shuttle-CNTF-R siRNA, both pRNA-U6.1/Shuttle-WSX-1 siRNA and pRNA-U6.1/Shuttle-CNTF-R siRNA (0.5 μg each), or pRNA-U6.1/Shuttle-FPR2 siRNA. The total amount of vectors was adjusted to be 1.0 μg by including a backbone vector. At 48 hrs after the transfection, the cells were added with HNG, CNTF or IL-27 and harvested 15 min later for immunoblot analysis with antibodies recognizing phosphotyrosine 705 of STAT3 or STAT3. The results are shown in photos.

FIGS. 12 (A)-(E)

A) F11 cells seeded on 6-well plate ($7 \times 10^4$ cells/well) were transfected with 1 μg of pRNA-U6.1/Shuttle vector or pRNA-U6.1/Shuttle-Bax. At 72 hrs after the transfection, the expression of mRNA of Bax was determined by real-time PCR. mRNA of G3PDH was determined as an internal control and used for calibration.

B) F11 cells seeded on 6-well plate ($7 \times 10^4$ cells/well) were transfected with pRNA-U6.1/Shuttle vector or pRNA-U6.1/Shuttle-Bax (0.5 μg or 1 μg). At 72 hrs after the transfection, the expression of Bax protein was determined by immunoblot analysis.

C) F11 cells seeded on 6-well plate ($7 \times 10^4$ cells/well) were transfected with 1 μg of pRNA-U6.1/Shuttle vector or pRNA-U6.1/Shuttle-Bax (1 μg). At 72 hrs after the transfection, the cells were added with 100 nM of Staurosporine (STS) or DMSO. The cell viability was determined by WST-8 assay after culture for 3, 6 and 9 hrs. The results obtained with respect to the cells treated with Vector/DMSO was taken as "100%" and used for calibration.

D) F11 cells seeded on 6-well plate ($7 \times 10^4$ cells/well) were transfected with 0.5 μg of pcDNA3 vector, pcDNA3-V642I-APP or pcDNA3-M146L-PS1 in association with 1.0 μg of pRNA-U6.1/Shuttle vector, pRNA-U6.1/Shuttle-Bax siRNA or pRNA-U6.1/Shuttle-WSX-1 siRNA. At 24 hrs after the transfection, the cells were added with 10 μM of HN, and subjected to WST-8 assay 72 hrs later. The expression of APP and PS1 was confirmed by immunoblot analysis with respect to parts of the cell lysate.

E) F11 cells on 6-well plate ($7 \times 10^4$ cells/well) were transfected with 1.0 μg of pRNA-U6.1/Shuttle vector, pRNA-U6.1/Shuttle-Bax siRNA, or both pRNA-U6.1/Shuttle-WSX-1 siRNA and pRNA-U6.1/Shuttle-CNTF-R siRNA (0.5 μg each). At 72 hrs after the transfection, the cells were added with an indicated amount of biotin-HN with or without unlabeled HN or HNA (100 μM) and subjected to an HN-binding assay based on immunofluorescence.

DETAILED DESCRIPTION

The Humanin receptor or Humanin-like polypeptide receptor (HNR) according to the present invention comprises at least two kinds of proteins selected from the group consisting of gp130 or its partial polypeptide, CNTF receptor a chain (CNTF-R) and WSX-1. Its examples include the receptor consisting of three proteins, i.e., gp130 or its partial polypeptide, CNTF-R and WSX-1, the receptor consisting of two proteins, i.e., gp130 or its partial polypeptide and WSX-1, and the receptor consisting of two proteins, i.e., CNTF-R and WSX-1. The receptor may further comprise other proteins as its constituent as long as they will never deteriorate the function of the receptor of the present invention.

Each subunit of the receptor such as gp130 or its partial polypeptide, CNTF-R and WSX-1 may be modified to have an amino acid sequence which comprises replacement, deletion, insertion and/or addition of one or more amino acids as long as such modification will not deteriorate the function of each subunit. These modified subunits may be prepared in any method known for those skilled in the art.

The "Humanin-like polypeptide" comprises a polypeptide and its derivative, which has suppressing or inhibiting function with a degree of the same or more than that of the polypeptide of 24 amino acids named Humanin disclosed in the International Publication No. WO01/021787 for neuronal cell death caused by AD-related insults. The "Humanin-like polypeptide (receptor)" in the present specification may also comprise "Humanin (receptor)" as well.

One of the examples of Humanin-like polypeptide is therefore a polypeptide having the amino acid sequence (1) disclosed in the International Publication No. WO01/021787:

(SEQ ID NO: 2)
Pro-Xaa-Xaa-Xaa-Xaa-Leu-Thr-Xaa-Xaa-Pro

Wherein the "Xaa" at position 3 means Cys or a basic amino acid, the "Xaa" at position 4 means Leu or Arg, the "Xaa" at position 8 means Gly or Ser, and the "Xaa" at positions 2, 5 and 9 means independently any amino acid sequence of ten or less amino acids.

More particularly, there may be further mentioned polypeptides disclosed in the International Publication No. WO01/021787, which have an amino acid sequence selected from the group consisting of SEQ ID NO: 5-8, 10, 12, 13, 21-24, 26-29, 32, 33, 37-40, 46, 48, 54 and 60 wherein one or more amino acids are replaced, deleted, inserted and/or added, and have a suppressing or inhibiting function for neuronal cell death caused by AD-related insults.

The above polypeptides include various kinds of derivatives. The "derivatives" means compounds in a modified form wherein their peptide functional group is modified, added, replaced or deleted by a conventional way. Such modification of the functional group may be performed by any known method for the purpose of protection of an existing functional group, stabilization of polypeptide or controlling of transition ability into tissues, controlling of polypeptide activity and the like.

Thus, the polypeptide may be modified naturally such as by post-translation modification, or artificially. Modification includes that of a backbone, an amino acid side chain, a terminal amino acid group, terminal carboxyl group, group and the like of peptide. The polypeptide may be a branched- or cyclo-one. The modification includes acetylation; acylation; ADP-ribosylation; amidation; covalent binding such as flavin, nucleotide, nucleotide derivative, lipid, lipid derivative or phosphatidyl inositol; formation of a cross-link; cyclization; formation of disulfide binding; demethylation; pyroglutamination; carboxylation; glucosylation; hydroxylation; iodization; methylation; myristoylation; oxidization; phosphorylation; ubiquitination and the like. Furthermore, the above polypeptide may be in a form of its salt or ester. The polypeptide may be synthesized according to a known synthetic technique, or prepared by expression of a DNA encoding said polypeptide.

The phrase "have a suppressing or inhibiting function for neuronal cell death caused by AD-related insults" in the present specification means being able to suppress or inhibit at least one kind of neuronal cell death related to AD. Thus, the above Humanin-like polypeptide includes a polypeptide that has a function of inhibiting at least one kind of neuronal cell death related to AD. The neuronal cell death may not be necessarily completely inhibited, but be significantly inhibited. The neuronal cell death may be determined by the method described in the following Example or by other methods such as that disclosed in the International Publication No. WO00/14204.

A compound that binds to the Humanin-like polypeptide receptor may be identified by the method for screening according to the present invention. The compound may be originally comprised in a living body such as human, or artificially synthesized. The compound may bind to any part of the Humanin-like polypeptide receptor, such as its intracellular domain or extracellular domain. The compound may be an agonist or antagonist for the receptor.

The screening method according to the present invention may be carried out in any known method or system such as a cell system or a cell-free system. The cell system uses cells per se that express the Humanin-like polypeptide receptor. As the proteins constituting the Humanin-like polypeptide receptor have been first revealed by the present invention, the cell in which the Humanin-like polypeptide receptor is compulsorily (constitutively) expressed may be prepared by any method known for those skilled in the art. For example, such cell may be easily obtained by transformation of an appropriate host cell with an expression vector comprising a gene encoding at least one of the proteins constituting the Humanin-like polypeptide receptor. By using such transformed cell, the binding characteristics between a compound comprised in a subject sample and the Humanin-like polypeptide receptor may be increased. As a result, even if only a small amount of a target compound is comprised in the subject sample, or if a binding capacity (affinity) of the compound is relatively small, its binding characteristics may be significantly determined.

The screening method of the present invention may be carried out by the following steps:
  (a) a step of placing a subject sample in contact with Humanin receptor or Humanin-like polypeptide receptor (HNR) or at least one protein that constitutes it;
  (b) a step of determining a binding characteristics between the receptor and the compound comprised in the subject sample; and
  (c) a step of selecting the compound that binds to the receptor.

By performing the step (a) in the presence of Humanin or Humanin-like polypeptide the binding characteristics of the compound may be determined by means of a competitive reaction between the compound and the Humanin or Humanin-like polypeptide.

In the screening method carried out in the cell system, the contact between the subject sample and the receptor may be realized by any method known for skilled in the art, such as adding the subject sample into a culture system of the cell expressing the receptor. In such cell system, the binding characteristics between the receptor and the compound is determined by detecting a change (increase, decrease or inhibition) in suppressing or inhibiting function for the neuronal cell death. Furthermore, the binding characteristics between the receptor and the compound may be determined by detecting increase or decrease of phosphorylation of tyrosine at 705 of STAT3.

The expression vector may be easily prepared by any method known for those skilled in the art. The gene encoding at least one of the proteins constituting the Humanin-like polypeptide may be easily prepared based on the disclosures of the International Publication No. WO01/021787 pamphlet and other known publications. The expression vector may comprise 5' and 3' non-coding regions such as, for example, a non-transcription sequence, non-translation sequence, promoter, enhancer, suppressor, transcription factor-binding sequence, splicing sequence, poly A—adding sequence, IRES, mRNA-stabilizing or destabilizing sequence in addition to a coding region of the protein.

There is no limitation on a kind of the host cell used in the screening method of the present invention, including cells or its bodies of mammalian such as human and monkey, plants, and insects. A host-vector system includes baculovirus-Sf cell system (Okamoto et al., J. Biol. Chem. 270:4205-4208, 1995), pcDNA-CHO cell system (Takahashi et al., J. Biol. Chem. 270:19041-19045, 1995), and CMV promoter-plasmid-COS sell system (Yamatsuji et al., EMBO J. 15:498-509, 1996). These cells may be cultured by any method known for those skilled in the art.

It is not necessary for such host cells originally express the HNR by themselves. However, the host cells may be prepared from tissues or cells that are supposed to express the receptor, such as brain cortex tissue, neuronal cell strains, neuroblastoma or teratoma. The neuronal cells include F11 cells, PC12 cells (L. A. Greene and A. S. Tischler, 1976, Proc. Natl. Acad. Sci. USA 73:2424-2428), NTERA2 cells (J. Skowronski and M. F. Singer, 1985, Proc. Natl. Acad. Sci. USA 82:6050-6054), and SH-SY5 Y cells (L. Odelstad et al., 1981, Brain Res., 224:69-82). In such cases, the compulsory expression of the receptor from the introduced expression vector would produce more amount of the HNR than originally expressed in these cells, promoting sensitivity of the detection well.

The screening method according to the present invention may be also carried out in the cell-free system by any method known for those skilled in the art. For example, the receptor or one of its constituting proteins may be used in its soluble form or a form immobilized or bound to a carrier depending on the screening method. The receptor of the present invention may be labeled with, for example, a radioactive isotope, fluorescent substance, biotin or digoxgenin, a tag sequence.

For example, the screening method may be carried out by placing the subject sample on an affinity column containing the HNR or one of its constituting proteins immobilized thereto, and purifying a compound that specifically binds to the column. Alternatively, the same method may be carried out by reacting a synthetic compound, natural product bank, or random phage peptide display library with the immobilized HNR or one of its constituting proteins. The screening may be made by using surface Plasmon resonance phenomenon (for example, manufactured by BIAcore Co.). These screening method may be carried out as a high through-put system be means of combinatory chemistry technique.

The subject sample to be used in the screening method according to the present invention includes a purified protein such as an antibody, an expressed product from a gene library, cell extract, supernatant obtained from cell culture, library of synthetic low-molecular compounds, natural materials such as soil, and cell-producing substances such as broth of actinomycetes. The subject sample may be optionally labeled with a radioactive isotope, fluorescent substance, etc.

Those skilled in the art may easily prepare a cell in which a gene encoding at least one protein that constitutes Humanin receptor or Humanin-like polypeptide receptor (HNR), which is selected from the group consisting of gp130, CNTF-R and WSX-1, is knocked out, by conventional gene-targeting technique. Such knockout cell is preferably a mammalian cell such as mouse and human cells. A knockout animal may be further generated by using these knockout cells according to any method known for those skilled in the art. The knockout animal may be heterozygous or homozygous. Especially, knockout rodents such as mouse or rat are useful as an experimental animal for researches of neurodegenerative diseases such as AD.

Since the compound that binds to Humanin receptor or Humanin-like polypeptide receptor (HNR) has an agonist or antagonist activity for the Humanin, it may be used in prevention or treatment of neurodegenerative diseases such as Alzheimer's disease (AD), amyotrophic lateral sclerosis (ALS), mad cow disease, vascular dementia (VD).

As prior studies have revealed that neuronal cell death occurs in AD, the pharmaceutical composition according to the present invention is expected be used as a medicine for protection of neurodegeration in AD. The pharmaceutical composition according to the present invention may be also used to prevent or treat diseases caused by neuronal cell death due to brain ischemia (T. Kirino, 1982, Brain Res., 239:57-69), Parkinsonism-dementia complex (PDC) (M. H. Polymeropoulos et al., 1997, Science, 276:2045-2047), Lewy bodies (M. G. Spillantini et al., 1998, Proc. Natl. Acad. Sci. USA, 95:6469-6473), and Down syndrome-related dementia. As APLP1, an analogous molecule of APP is thought to be a causative gene of congenital nephrosis syndrome (Lenkkeri, U. et al., 1998, Hum. Genet. 102:192-196), renal diseases such as nephrosis syndrome may be a target of prevention or treatment by the pharmaceutical composition according to the present invention.

The pharmaceutical composition according to the present invention comprises the compound that can bind to the HNR as an effective component may be directly administered into a patient, or formulated by known formulation methods optionally with, for example, a pharmaceutical carrier or solvent such as sterilized water, physiological saline, vegetable oil, emulsifier, suspending agent, surfactant, stabilizer, and slow-releasing agent. The pharmaceutical composition according to the present invention may be in a form of aqueous solution, tablet, capsule, troche, buccal tablet, elixir, suspension, syrup, nasal solution, or inhalant liquid. The content of the effective component may be optionally determined by those skilled in the art, depending on the purpose of the treatment, administration route, subject to be treated and the like.

The pharmaceutical composition according to the present invention may be administered transdermally, transnasally, transbronchially, intramuscularly, intraperitoneally, intravenously, through spinal foramen or cerebral ventricle or orally, depending on the features of the component. In the treatment of cerebral neurodegenerative diseases, the pharmaceutical composition according to the present invention may be preferably introduced into central nerve system through an appropriate route such as an intravenous, through spinal foramen or cerebral ventricle and intradural injection. Those skilled in the art may select an appropriate dose depending on the age, weight and conditions of disease of a patient and the administration route and the like. The dose and the administration route may be in turn optionally selected by those skilled in the art depending on tissue-transition ability of the effective component, the purpose of treatment, the age, weight and conditions of disease of a patient and the like. In the administration of the pharmaceutical composition according to the present invention for the purpose of protection of cerebral neurodegeneration such as in AD disease, the composition is preferably administered in such an amount as to effectively inhibit neurodegeneration around target cells. Thus, Humanin polypeptide or other substances showing an equivalent protecting function for neuronal cell death may be administered in an amount of at least 1 nM, preferably 10 nM or more, more preferably 100 nM or more, further preferably 1 µM or more.

The antibody according to the present invention may be in any forms or kinds known for those skilled in the art, including polyclonal antibodies and monoclonal antibodies, and various kinds of chimeric antibodies such as a humanized one, which may be prepared by any genetic engineering method known for those skilled in the art.

EXAMPLES

The present invention will be further explained more in detail by referring to the following examples, which should not be construed to limit a technical scope of the invention.

Materials And Methods

Cell lines And genes

Neurohybrid F11 cells and pcDNA3 vectors encoding V642I-APP, K595N/M596L-APP (NL-APP), M146L-PS1, and N141I-PS2 cDNA were prepared as already described (Hashimoto et al, 2000, 2001a, 2003). pCAG-human gp130 and pCAG-human gp130 ED (the extracellular domain of human gp130) were prepared as described (Kumanogoh et al., 1997). pcDNA3 vectors encoding the extracellular domain of the G-CSF receptor fused to the full-length transmembrane domain and various portions of the intracellular domains of human gp130, were prepared as described (Fukada et al, 1996). The intracellular domain of gp130 was C-terminally truncated. A chimera protein named G-277 contained a 277 amino acid-long full intracellular domain of gp130 (SEQ ID NO:35), while G-195, G-133, G-68, and G-25 contained the amino acids 1-195 (SEQ ID NO:36), 1-133 (SEQ ID NO:37), 1-68 (SEQ ID NO:38), and 1-25 (SEQ ID NO:39) intracellular portions, respectively. C-terminally myc-tagged human WSX-1 and myc-tagged mouse CREME9 cDNAs were amplified from human and mouse embryo cDNA (BioChain) by PCR using sets of sense primers and antisense primers: 5'-ACTAGTACCATGCGGGGAGGCAGGGG-3' (SEQ ID NO:3) and 5'-GAATTCGGCCAGAACCTGTGGCCTGG-3' (SEQ ID NO:4) for human WSX-1; 5'-GGATCCACCATGAAGGGCGCGATGGAGCC-3' (SEQ ID NO:5); and 5'-GAATTCAAATACCAGCACTTTCCATCCAGG-3' (SEQ ID NO:6) for mouse CREME9. Plasmids encoding C-terminally V5-tagged human CNTF-R (V%-CNTF-R) and rat IL-6R (pUCM18-rat IL-6R) were purchased from Invitrogen and American Culture Collection, respectively. A pEFBos vector comprising familial ALS (FALS) gene G85R-SOD1 was kindly provided by Dr. Shoji Tsuji. Cosmid of human wild gp103 was constructed by inserting a full-length gp130 into a SwaI site of pAxCAwt (TaKaRa).

Recombinant Cytokines And Soluble Receptor

Mouse cardiotropin-1 (CT-1), rat IL-6, rat IL-11, soluble rat IL-6R, soluble human CNTF-R, recombinant mouse gp130/Fc chimera and recombinant human soluble CNTF-R were purchased from R & D systems (Minneapolis, Minn., USA). Human IL-6, human oncostatinM (OSM), rat CNTF, human GCSF were purchased from Peprotec EC, Ltd. (London, UK). Human CNTF was purchased from R&D Systems or mouse LIF, mouse IL-11, or soluble rat CNTF-R were purchased from R & D systems or Peprotec EC, Ltd.

Antibody

Anti-mouse APP antibody (22C11) and anti-mouse PS1 antibody were purchased from Chemicon (Temecula, Calif., USA). Anti-PS2 antibody and phosphor STAT3 (Tyr$^{705}$) antibody were purchased from Cell Signaling Technology (Beverly, Mass., USA). Anti-myc monoclonal antibodies with or without HRP were purchased from Biomol (Plymouth Meeting, Pa.). Anti-V5 with or without HRP was purchased from Invitrogen. Rabbit polyclonal anti-HN antibody PO4 was raised as described (Tajima et al., 2002). Antibodies against G-CSFR, gp130, CNTF-R, LIFR, SOD1, ATAT3, IL-6R were purchased from Santa Cruz Biotechnology (Santa Cruz, Calif., USA). Anti-phosphotyrosine monoclonal antibody 4 G10 was purchased from Upstate USA (Charlottesville, Va., USA). Two rabbit polyclonal antibodies and anti-mouse WSX-1 antibody were obtained by immunization with a synthetic peptide: MNRLRVARLTPLELLL (mWSX-1-N; SEQ ID NO:7) corresponding to N-terminal 16 amino acids of WSX-1 and a synthetic peptide: YSGYEKHFLPTPEELGLLV (mWSX-1-C; SEQ ID NO:8) corresponding to C-terminal 16 amino acids of WSX-1 that were covalently bonded to keyhole limpet hemocyanin (Sigma). Similarly, two rabbit polyclonal anti-human WSX-1 antibodies were obtained by immunization with a synthetic peptide: MRGGRGAPFWLWPLPKC (hWSX-1-N; SEQ ID NO:9) corresponding to N-terminal 17 amino acids of WSX-1 and a synthetic peptide: LPTPEELGLLGPPRPQVLAC (hWSX-1-C; SEQ ID NO:10) corresponding to C-terminal 20 amino acids of WSX-1 that were covalently bonded to keyhole limpet hemocyanin (Sigma). Anti-mouse gp130 neutralizing antibody, anti-mouse LIFR neutralizing antibody, anti-mouse IL-11R neutralizing antibody, anti-human CNTF-R neutralizing antibody, and anti-rat CNTF-R neutralizing antibody were purchased from R & D Systems. The other monoclonal antibodies, anti-mouse gp130 antibody RX435 were kindly provided by Dr. Hiroshi Hukuda of Keio University School of Medicine. Anti-Bax antibody was purchased from Santa Cruz Biotechnology (P-19).

Peptides

Synthetic Humanin (HN), synthetic S14 G-Humanin (HNG), C8A-Humanin (HNA), and human amyloid-□ (1-42) peptide were from purchased Peptide Institute, Inc. (Minoh, Osaka, Japan). Biotin-HN and Biotin-HNG were purchased from KNC Laboratories Co., Ltd.

Transfection, Cell Death Assay, And Cell Viability Assay

The transfection procedures were as described (Hashimoto et al, 2000, 2001a, 2003). F11 cells, seeded at 7×10$^4$/well in 6-well dishes, were transfected with indicated vectors. Transfection efficiency in these protocols has been determined to be invariably around 70%. At 72 hrs after transfection, the Trypan blue exclusion assay and LDH assay were performed as a cell-death assay and the WST-8 assay was performed as cell-viability assays (Hashimoto et al, 2000, 2001a b, 2003). HN was added to the culture medium usually at 5 hrs after transfection, but in some cases at 24 hrs after transfection.

Primary Cortical Neurons And Cell Viability Assays

The primary culture of mouse cortical neurons was prepared as described previously (Sudo et al., 2000). Briefly, primary cortical neurons, obtained from embryonic day 14 (E14) ICR mice were seeded in poly-L-lysine-coated 96 well plates (Sumitomo Bakelite) at 2.5 or 5.0×10$^4$ cells/well in Neuron Medium (Sumitomo Bakelite) (Hashimoto et al., 2003; Niikura et al., 2004). Purity of neurons by this method was >98%. After 3 days, the culture medium was replaced with DMEM with N2 supplement. On the fourth day in vitro, 25 μM of Aβ (1-42) was added in association with indicated concentrations of HN or cytokines in the presence or the absence of soluble cytokine receptors or neutralizing antibodies. At 72 hrs after the onset of treatment, cell viability was assessed by WST-8 assay and/or Calcein fluorescence assay and cell mortality was assessed by the Trypan blue exclusion assay and LDH assay (Hashimoto et al, 2000, 2001 a b, 2003).

Immunofluorescence-Based Binding Assay (1)

F11 cells (7×10$^4$/well in 6-well plates) were replated into 96-well plates (7×10$^3$ cells/well) at 24 hrs after transfection with indicated amounts of the plasmids encoding mycHis-WSX or V5-CNTF-R, and with PCAG-human gp130 if required. At 36 hrs after transfection, the cells were added with 100 nM of biotin-labeled HNG-FLAG in the presence or the absence of 10 μM of HNG (S14 G-HN) or HNA (C8A-HN) (Hashimoto et al., 2001a). After 6 hrs incubation, they were fixed with 4% paraformaldehyde in PBS for 30 min. After washing with PBS, cells were stained with FITC-conjugated avidin (Molecularprobe, Eugene, Oreg., USA). Immunofluorescence intensity was measured (excitation=485 nm, emission=535 nm) with a spectrofluorometer (Wallac1420 ARVOsx Multi Label Counter). Immunohistochemical analysis was done with a laser-scanning, confocal microscope LSM (Carl Zeiss, Germany).

Immunofluorescence-Based Binding Assay (2)

F11 cells (7×10$^4$/well in 6-well plates) were replated into 96-well plates (7×10$^3$ cells/well) at 24 hrs after transfection with indicated amounts of the plasmids encoding mycHis-WSX or V5-CNTF-R, and with PCAG-human gp130 if required. At 36 hrs after transfection, the cells were added with biotin-labeled HN or HNG of indicated concentrations in the presence or the absence of HNG (S14G-HN) or HNA (C8A-HN) of indicated concentrations (Hashimoto et al., 2001 a). After 6 hrs incubation, they were fixed with 4% paraformaldehyde in PBS for 30 min. After washing with PBS, cells were stained with FITC-conjugated avidin (Molecularprobe, Eugene, Oreg., USA). Immunofluorescence intensity was measured (excitation=485 nm, emission=535 nm) with a spectrofluorometer (Wallac1420 ARVOsx Multi Label Counter). Immunohistochemical analysis was done with a laser-scanning, confocal microscope LSM (Carl Zeiss, Germany).

Pull-Down Assays

F11 cells (7×10$^4$/well in 6-well plates) were transfected with the plasmids encoding mycHis-WSX-1, V5-CNTF-R or rat IL-6R (V6 tagged). At 48 hrs after transfection, the cells were harvested for pull-down assays with HN or HNA-conjugated Sepharose 4B. For conjugation of HA or HNA with Sepharose 4B, 3 ml of CNBr-activated Sepharose 4B was incubated with 0.5 mg of HN or HNA in a coupling buffer (0.1M NaHCO$_3$ 0.5M NaCl, pH8.3) overnight at 4° C. The beads were then reacted with a blocking buffer (0.2M glycine, pH 8.0) for 2 hrs at a room temperature, washed with the coupling buffer and stored at 4° C. for use in pull-down assay. For each pull-down assay, 20 μl of 1:1 slurry of Sepharose was used for 100 μl of the cell lysate.

Immunoblot Analysis

Cell lysates (10-20 μg/lane) or pulled-down precipitates were subject to SDS-PAGE, and the proteins separated on the gel were transferred onto polyvinylidene difluoride membranes as described (Hashimoto et al, 2000). Visualization of the immunoreactive protein bands was performed by ECL (Amersham Pharmacia Biotech, Uppsala, Sweden).

Plasmid-Based Small Interfering RNA

Plasmid vectors encoding small interfering RNA (siRNA) for mouse FPR2, mouse CNTF-R, mouse WSX-1, mouse IL-6R and mouse LIFR were constructed as follows. The sense and antisense DNA fragments used for the construction were as follows:

| Mouse FPR2 |
|---|
| Sense DNA fragment:<br>(SEQ ID NO: 11)<br>5'-AGGATCCCGTAACTACCACCTAAGCAATGTCTTGATATCCGGACAT<br>TGCTTAGTGGTAGTTATTTTTTCCAAAAGCTTGCA-3', and |
| Antisense DNA fragment:<br>(SEQ ID NO: 12)<br>5'-TGCAAGCTTTTGGAAAAAATAACTACCACTAAGCAATGTCCGGATA<br>TCAAGACATTGCTTAGTGGTAGTTACGGGATCCT-3'; |

| Mouse CNTF-R |
|---|
| Sense DNA fragment:<br>(SEQ ID NO: 13)<br>5'-TTGGATCCCGTGTGTGCTGTGCCATCCGAGATTGATATCCGTCTCG<br>GATGGCACAGCACACATTTTTTCCAAGGTACCTT-3', and |
| Antisense DNA fragment:<br>(SEQ ID NO: 14)<br>5'-AAGGTACCTTGGAAAAAATGTGTGCTGTGCCATCCGAGACGGATAT<br>CAATCTCGGATGGCACAGCACACGGGATCCAA-3'; |

| Mouse WSX-1 |
|---|
| Sense DNA fragment:<br>(SEQ ID NO: 15)<br>5'-TTGGATCCCATATCCACTTGAGAGAAGATCTTGATATCCGGATCTT<br>CTCTCAAGGGATATTTTTTCCAAGGTACCTT-3', and |

-continued

Antisense DNA fragment:
(SEQ ID NO: 16)
5'-AAGGTACCTTGGAAAAAAATATCCACTTGAGGAAGATCCGGATATC

AAGATCTTCTCTCAAGTGGATATGGGATCCAA-3';

Mouse IL-6R

Sense DNA fragment:
(SEQ ID NO: 17)
5'-GCGGATCCCGTTTAAGCTGTGAAACGCTTCGTTGATATCCGCGAAG CGTTTCACAGCTTAAATTTTTTCCAAAAGCTTGC-3', and Antisense DNA fragment:
(SEQ ID NO: 18)
5'-GCAAGCTTTTGGAAAAAATTTAAGCTGTGAAACGCTTCGCGGATAT

CAACGAAGCGTTTCACAGCTTAAACGGGATCCGC-3';

Mouse LIFR

Sense DNA fragment:
(SEQ ID NO: 19)
5'-TTGGATCCCATATCCACTTGAGAGAAGATCTTGATATCCGGATCTT CTCTCAAGGGATATTTTTTTCCAAGGTACCTT-3', and Antisense DNA fragment:
(SEQ ID NO: 20)
5'-AAGGTACCTTGGAAAAAAATATCCACTTGAGGAAGATCCGGATATC

AAGATCTTCTCTCAAGTGGATATGGGATCCAA-3';

Mouse Bax

Sense DNA fragment:
(SEQ ID NO: 21)
5'-CGGGATCCCATGATCTGTTCAGAGCTGGTGTTGATATCCGCACCAG CTCTGAACAGATCATTTTTTTCCAAGGTACCCC-3', and Antisense DNA fragment:
(SEQ ID NO: 22)
5'-GGGGTACCTTGGAAAAAAATGATCTGTTCAGAGCTGGTGCGGATAT

CAACACCAGCTCTGAACAGATCATGGGATCCCG-3'.

These DNA fragments were annealed by heating and cooling according to the manufacturer's instruction. These annealed primers and the pRNA U6.1/Shuttle empty vector (GenScript, NJ, USA) were digested by BamHI and KpnI at 37° C. overnight. The digested DNA fragments and the empty vectors were purified by GENE CLEAN II kit (Q BIOgene, USA). Ligation was performed with Ligation Convenience Kit (NIPPON GENE, Tokyo, Japan) according to the manufacturer's instruction. The sequence of these siRNA vectors was confirmed by a direct sequencing, and effects of these siRNA plasmids were confirmed by real-time PCR as described below.

Real-Time PCR

We performed real-time PCR to assess the amount of endogenous mRNA. Cells were harvested for RNA extraction with ISOGEN reagent (Nippon Gene, Toyama, Japan) followed by real-time PCR. The first-strand cDNAs were synthesized using Sensiscript reverse transcriptase (QIAGEN, Germany) with 0.5 mg total RNA. Real-time PCR analysis was performed using a QuantiTect SYBR Green PCR kit (QIAGEN), followed by analysis with ABI PRISM7700 (Applied Biosystems, Foster City, Calif.). We made sets of a sense primer and an antisense primer as follows:

Mouse CNTF-R
5'-TTCCACCGTGACTCCTGCACCTG-3',
and

5'-GAGGGCTGGGTCCTTCTCACAGAC-3'

Mouse WSX-1
5'-CCGCAGAAAGCTCTCACCTGTCAG-3',
and

5'-CCATGGATATCCGTTCTCCACCTG-3'

Mouse LIF-R
5'-GTGGAAGATACGTCGGCAGACTCG-3',
and

5'-ACCCTGAAGGTCAGCAATCCTCAG-3'

Mouse IL-6R
5'-CCCTGCCAGTATTCTCAGCAGCTG-3',
and

5'-CGGCCTTCCAGGTATGGCTGATAC-3'

Mouse Bax
5'-GGAATTCACCATGGACGGGTCCGGGGAGCAG-3',
and

5'-GGGGTACCGCCCATCTTCTTCCAGATGGTGAG-3'

Human and Mouse G3PDH
5'-TCCACCACCCTGTTGCTGTA-3'
and

5'-ACCACAGTCCATGCCATCAC-3'.

Data analysis was performed using a software Sequence Detection System ver. 1.9.1 (Applied Biosystems). To adjust the expression level of each mRNA, G3PDH mRNA was used as an internal control.

Statistical Analyses

All cell-death (mortality) experiments, cell viability experiments, and real-time PCR experiments were done with n=3. All values in the figures of the in vitro study are mean±SD. Statistical analysis was performed with analysis of variance followed by post hoc test, in which $p<0.05$ was assessed as significant.

Result 1

Considering that certain tyrosine kinases as well as STAT3 are involved in HN-mediated neuroprotection (Hashimoto et al. 2005), we suspect that the HN receptor belongs to a cytokine receptor family. Gp130 is a cytokine receptor subunit common to the cytokine receptors belonging to the IL-6 receptor family. As shown in FIGS. 1A and 1B, enforced expression of the extracellular domain and the transmembrane domain of human gp130 (gp130 tr) or addition of recombinant soluble human gp130 consisting of the extracellular domain of human gp130 (gp130ED), resulted in complete suppression of HN-mediated neuroprotection against toxicity by overexpressed V642I-APP(A) and 25 μM of Aβ (B). Because gp130 tr and gp130ED has been demonstrated to act a dominant-negative form of gp130 (Kumanogoh et al., 1997; Jostock et al. 1998), this finding indicated that HN-mediated neuroprotective signal is mediated by gp130. We then tested how treatment with neutralizing anti-gp130 antibody would modify HN-mediated signals in order to confirm this finding. Antibodies to mouse gp130 (RX435), which has been shown to inhibit mouse gp130 function, but not human gp130, attenuated HN-mediated neuroprotection (FIG. 1C)

while such inhibition was suppressed by simultaneous ectopic expression of human gp130 in F11 cells (FIG. 1D), clearly indicating that gp130 is involved in HN-mediated signals.

Result 2

To further confirm the involvement of gp130 in HN-mediated neuroprotective signals, we constructed various chimera proteins consisting of the extracellular domain of the G-CSF receptor fused to the full transmembrane domain of gp130 and various-length intracellular domains of gp130 systematically C-terminally truncated (Fukada et al., 1996). A chimera protein named G-277 contained a 277 amino acid-long full intracellular domain of gp130 (SEQ ID NO:35), while G-195, G-133, G-68, and G-25 contained the amino acids 1-195 (SEQ ID NO:36), 1-133 (SEQ ID NO:37), 1-68 (SEQ ID NO:38), and 1-25 (SEQ ID NO:39) intracellular portions, respectively. (The N-terminal amino acid in the intracellular domain is considered as No. 1). At first, the expression of these chimera proteins was confirmed (FIG. 2A). Stimulation with 100 nM G-CSF prevented neuronal cell death induced by ectopic expression of V642I-APP when G-277 was expressed. On the other hand, the same stimulation did not prevent V642I-APP mediated neuronal cell death when either G-25 or G-68 was expressed (FIG. 2B). Intermediately, stimulation with 100 nM G-CSF partially prevented V642I-APP-mediated neuronal cell death when G-133 was expressed (FIG. 2B). Because it was already shown in the previous study that the third tyrosine from the membrane of the intracellular domain of gp130, which is contained in G-133, was essential for anti-apoptotic effect in proB cells (Fukada et al., 1996), we speculated that other signal mediated by the amino acids 134-277 (amino acids)-corresponding part of the intracellular domain of gp130 was required for the full protection of neuronal cell death by AD-related insults. Similarly, stimulation with 100 nM G-CSF prevented NL-APP-, M146L-PS1-, N141I-PS2-mediated neuronal cell death when G-277 was expressed, but not when G-25 was expressed (FIG. 2C). In contrast to these AD-related neuronal cell death, stimulation with 100 nM G-CSF did not prevent neuronal cell death induced by overexpression of the mutant Cu/Zn-superoxide dismutase genes, which has been shown to cause familial amyotrophic lateral sclerosis, a representative motoneuron-specific neurodegenerative disease (FIG. 2D). Furthermore, the treatment with HN increased phosphorylation level of gp130 (FIG. 2E).

Result 3

Figure 3:
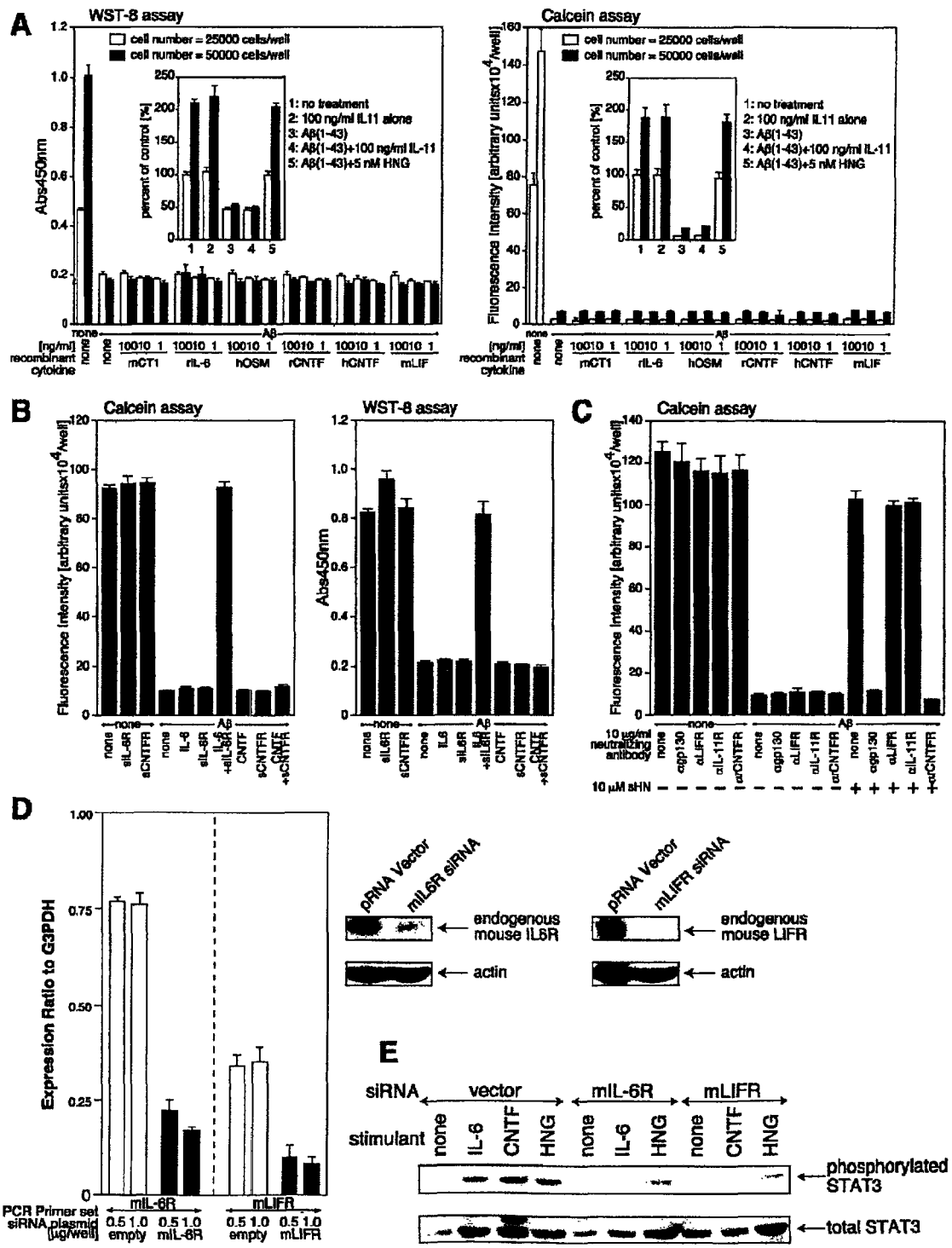

In order to search a molecular basis of the HN receptor, we tested whether or not known cytokines belonging to IL-6 families could mimic the HN-mediated neuroprotection. As shown in FIG. 3A, treatment with either physiological levels (up to 100 ng/ml) of mouse cardiotropin-1 (CT-1), rat IL-6, mouse IL-11, human OncostatinM (OSM), mouse Leukemia-inhibitory factor (LIF), or human Ciliary Neurotrophic Factor (CNTF) that could bind and stimulate mouse cognate receptors, did not inhibit neurotoxicity by Aβ in F11 cells. This was true for neurotoxicity by overexpression of V642I-APP (similar data not shown).

Because IL-6 receptor, IL-11 receptor, the LIF receptor, the CNTF receptor, and gp130 were expressed in F11 cells as well as primary cortical neurons (PCNs) (unpublished observation by Y. H. and M. M.), the functional IL-6, IL-11, OS, LIF, and CNTF-R must have been generated in these neuronal cells by combination of these receptor subunits. Accordingly, we concluded that IL-6-, IL-11-, CT-1-, OSM-, LIF-, and CNTF-induced activation of gp130-mediated pathways was insufficient for protection against neuronal cell death by AD-related insults. These findings were against the possibility that HN would elicit neuroprotection by binding to these receptors.

Result 4

To increase IL-6-mediated signal, we examined the effect of addition of the soluble IL-6 receptor a or the soluble CNTF receptor a (sIL-6R) (100 ng/ml) in association with treatment with IL-6 or CNTF (100 ng/ml) on neuronal cell death by Aβ (FIG. 3B). Either IL-6 completely mimicked HN in neuroprotection in the presence of overexpression of sIL-6R, indicating that enhancement of IL-6-induced homodimerization of gp130 mimics the HN activity. In contrast, CNTF did not mimic HN even in the presence of overexpression of the soluble CNTF receptor. Considering that CNTF binding to the CNTF receptor induced heterodimerization between gp130 and the LIF receptor so as to trigger the intracellular signal cascade, we speculated that the LIF receptor was not involved in HN-mediated neuroprotection.

Result 5

Using neutralizing antibodies to gp130-coupled receptors, we further examined whether or not known gp130-coupled receptors participated in HN-mediated neuroprotection. We then found that a neutralizing antibody to the rat CNTF receptor, which was speculated to also recognize mouse CNTF receptor, was able to nullify the HN activity (FIG. 3C). Combined with the foregoing finding about the CNTF/soluble CNTF receptor in FIG. 3B, we suspected that the CNTF receptor was involved in HN signals in a manner quite different from the way in which association between CNTF and CNTF-R facilitated the heterodimerization of gp130 and the LIF receptor. We further constructed vectors encoding siRNA specific to IL-6R and LIF-R, respectively (FIG. 3D). The decrease of expression of endogenous IL-6R or LIF-R due to the expression of these vectors in F11 cells did not attenuate phosphorylation of STAT3 (FIG. 3E), showing that HN did not transduce cell viability signal through IL-6R or LIF-R.

Result 6

In search for molecular basis of the HN receptor as a putative gp130-coupled receptor complex, we have further tested the recently identified IL-27 receptor WSX-1 (Specher et al., 1998), which appear to be a gp130-coupled receptor (Planz et al., 2004), and an uncharacterized putative gp130-coupled receptor, CREME9 (CRL4) (Boulay et al., 2003) by an immunofluorescence-based HN binding assay (1) after ectopic overexpression of these genes together with human gp130 in F11 cells. This assay was not sensitive enough to detect association between HN and the endogenous HN receptor.

Figure 4:
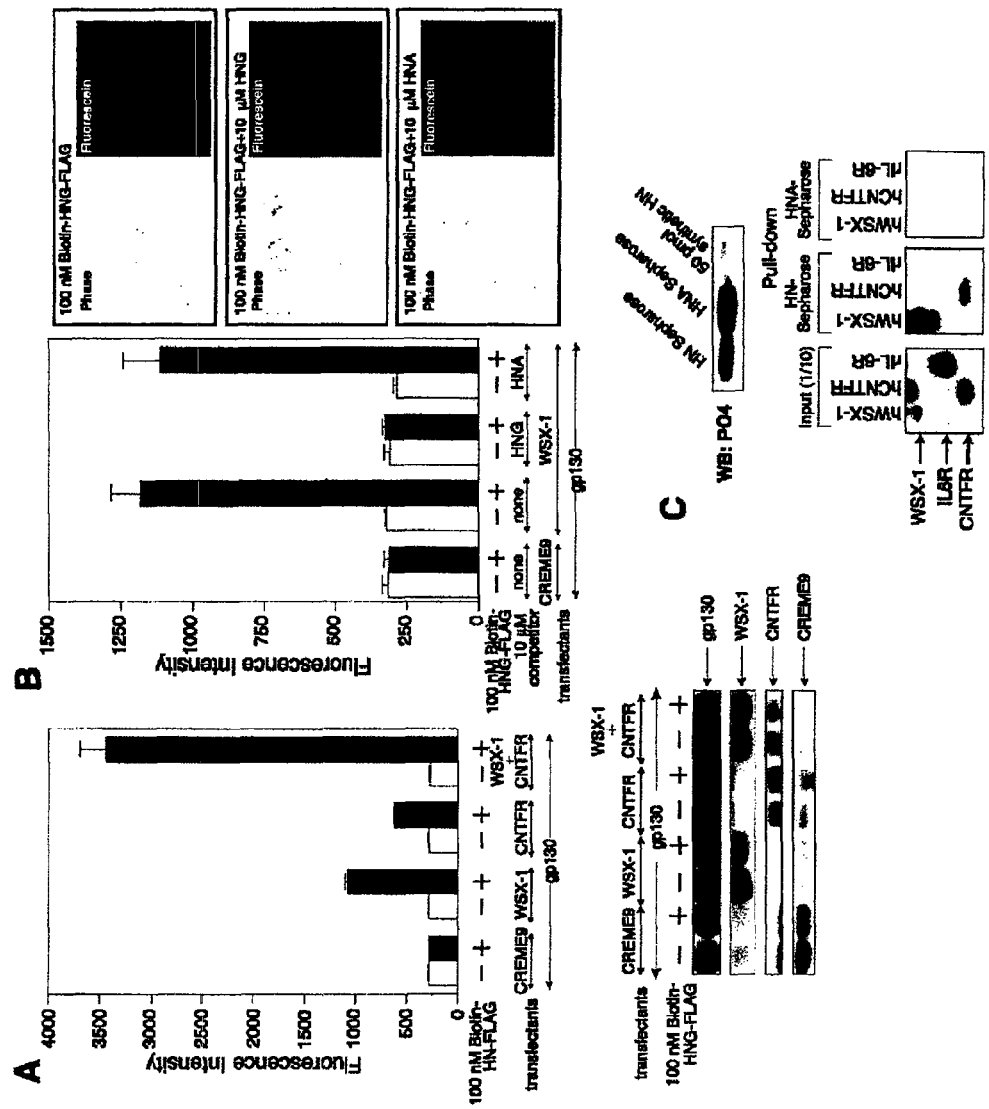

We found that expression of human WSX-1 or the human CNTF receptor in F11 cells increased the binding of HN to the F11 cells while expression of CREME9 did not (FIG. 4A). We further found that overexpression of both the CNTF receptor and WSX-1 resulted in synergistic increase in binding of HN to the F11 cells (FIG. 4A), suggesting that both the CNTF receptor and WSX-1 were components of the HN receptor. The expression of each protein was confirmed by immunoblot analysis. To confirm that HN specifically associated with WSX, we performed an HN-binding experiment in the presence of a large amount of HN-G, a 1000-fold potent HN derivative, or HN-A, an HN mutant with null activity as a negative control (Hashimoto et al., 2001a) (FIG. 4B). Apparently, HN-G, but not HN-A, nullified the binding of HN to cells expressing WSX-1 and gp130, confirming the presence of a specific binding between HN and WSX-1. Using the in vitro pull-down assays with HN (or HN-A) covalently immobilized onto Sepharose 4B beads, we further confirmed that HN bound to the CNTF receptor and WSX-1, but not to the IL-6 receptor in the lysates prepared from F11 cells overexpressing CNTF-R or WSX-1 (FIG. 4C). On the other hand, it was confirmed that HNA did not bind to these receptors (FIG. 4C).

Result 7

Figure 5:
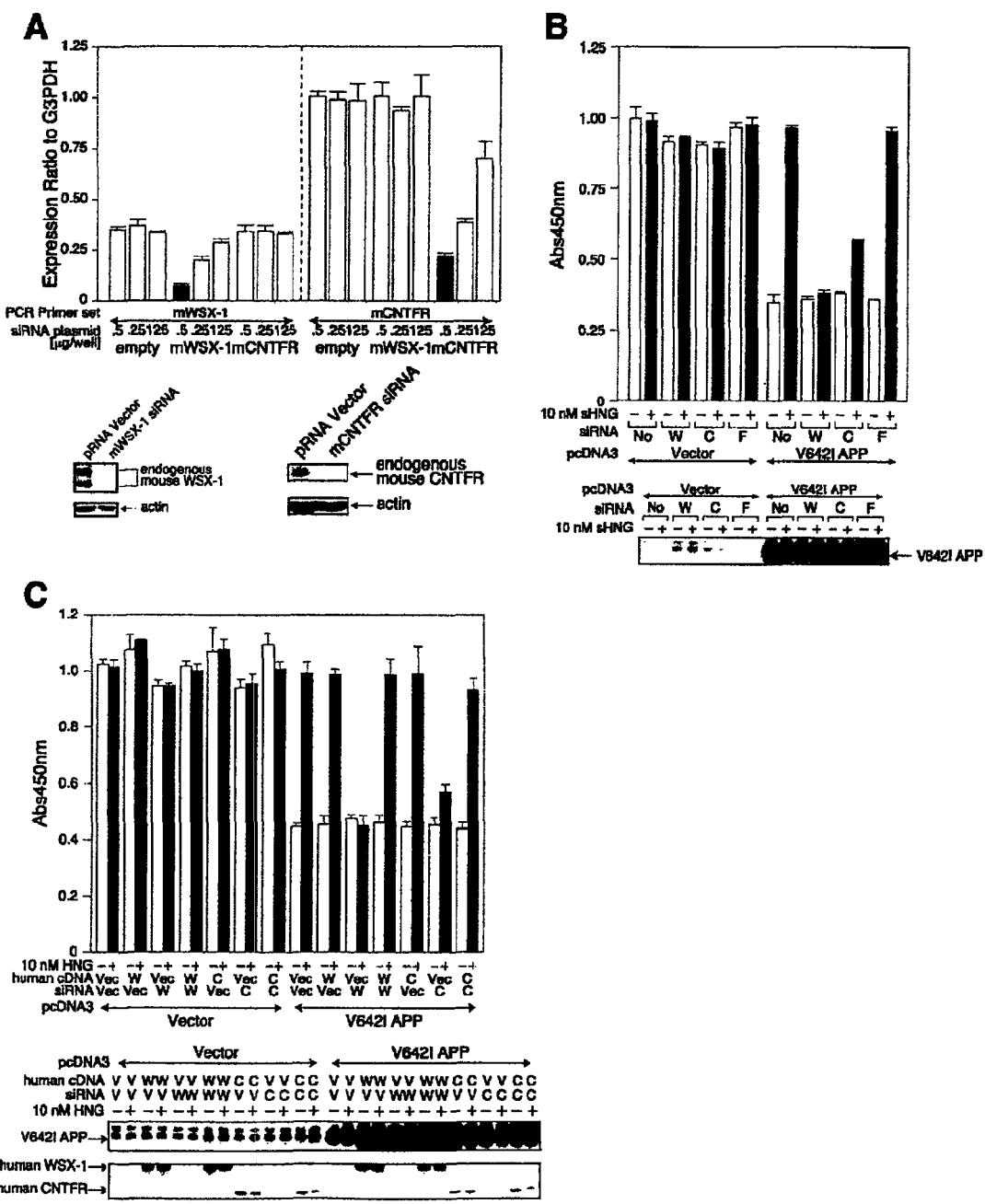

To confirm the involvement of the CNTF receptor and WSX-1 in the HN-mediated neuroprotective signal, we knocked down expression of these proteins by using a plasmid-based siRNA-mediated disruption technique. The efficacy of this method was confirmed by measurement of mRNA with real-time PCR (Sui et al., 2001; Kanekura et al., 2004) (FIG. 5A). As a negative control, we tested siRNA for mouse FPR-2 (Hashimoto et al., 2005), a putative HN receptor (Ying et al., 2004). As shown in FIG. 5B, disruption of the endogenous WSX-1 almost completely suppressed the HN activity against neurotoxicity by overexpression of V642I-APP. Disruption of the CNTF receptor reduced the HN activity by 30% compared with the control while disruption of FPR-2 did not reduce the HN activity. Furthermore, coexpression of human CNTF receptor or human WSX-1 completely recovered the HN activity, which had been inhibited by siRNA for the mouse CNTF receptor or mouse WSX-1 (FIG. 5C), strongly supporting the notion that the CNTF receptor and WSX-1 were components of the HN receptor. Considering that treatment with the neutralizing antibody to the CNTF receptor completely antagonized the HN activity (FIG. 3C) while siRNA-mediated disruption of the CNTF receptor appeared incomplete compared with that of WSX-1 (FIG. 5A), we suspected that incomplete disruption of expression of the CNTF receptor could result in incomplete inhibition of the HN activity in FIG. 5B.

Result 8

Figure 6:
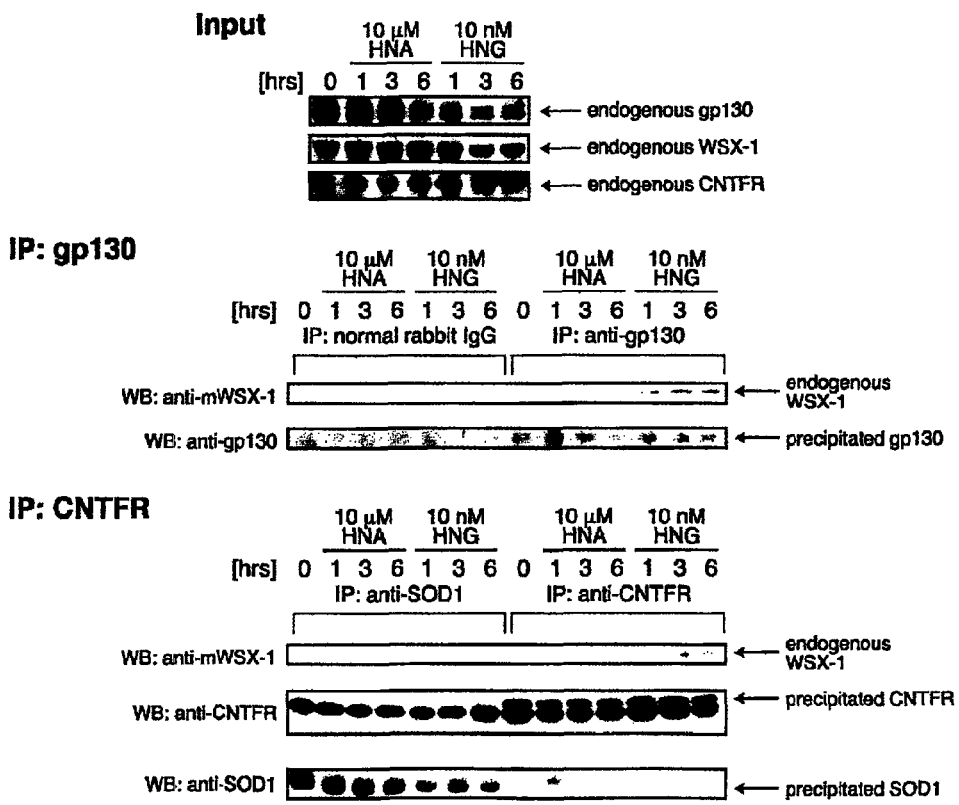

We then tested whether or not CNTF-R could make a complex with WSX-1. To address this issue, we overexpressed myc-tagged human WSX-1 and V5-tagged human CTNFR in COST cells and performed co-immunoprecipitation analysis. As shown in FIG. 6A, immunoprecipitation of WSX-1 co-precipitated CNTF-R and immunoprecipitation of CNTF-R co-precipitated WSX-1, indicating that WSX-1 could associate with CNTF-R.

Result 9

The HN treatment induced the association between CNTF-R and WSX-1, or between WSX-1 and gp130. As shown in FIG. 6B, F11 cells were harvested at 0, 1, 3 and 6 hrs after the treatment with 10 nM of HNG or HNA and subjected to immunoprecipitation analysis with the anti-gp130 antibody or anti-CNTF-R antibody. The resulting precipitates were then subjected to immunoblot analysis with the anti-mWSX-1 antibody. The results showed that the HN treatment would specifically induce the association between CNTF-R and WSX-1 and between WSX-1 and gp130 at an endogenous expression level.

Result 10

Figure 7:
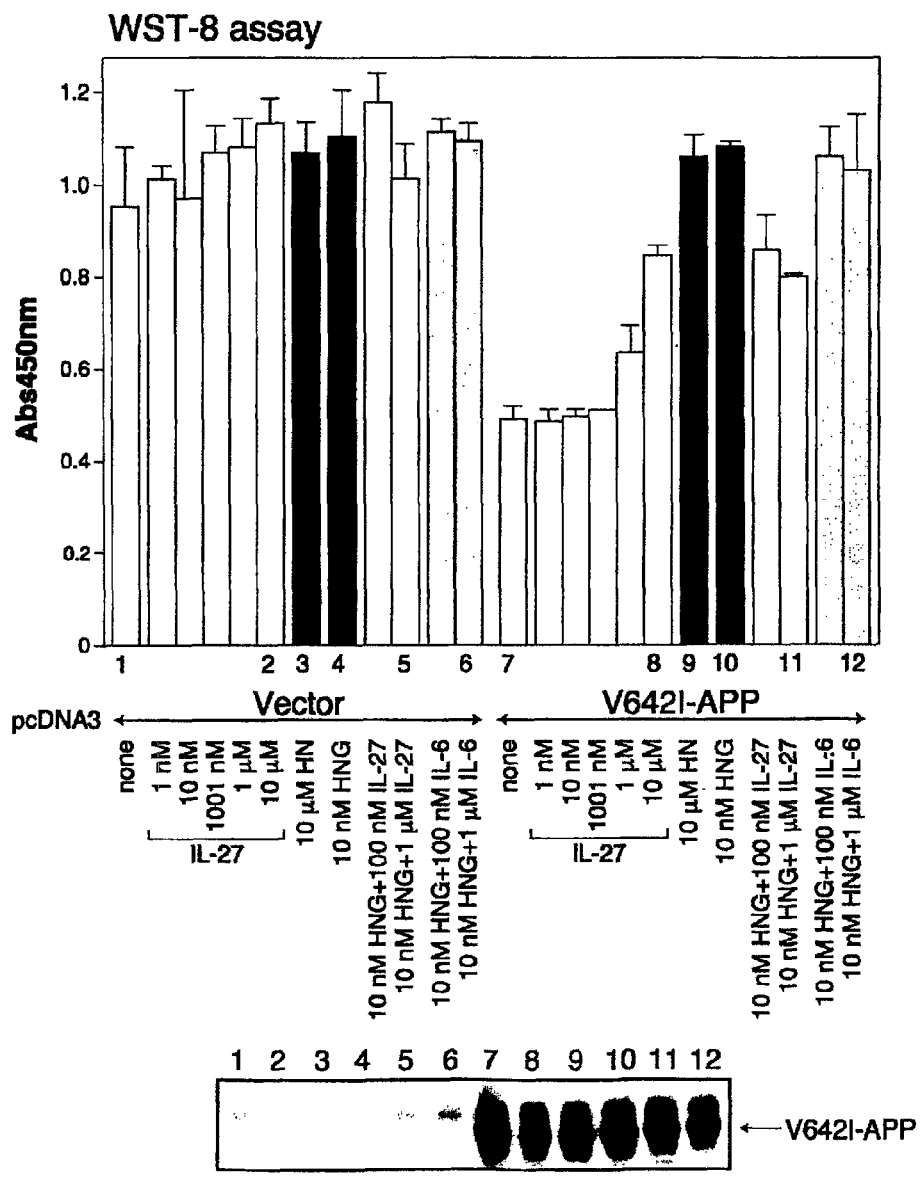

It had been already known that WSX-1/gp130 functioned as a receptor of IL-27, indicating the possibility that IL-27 could show the same effect as HN. As expected, the IL-27 treatment showed HN-like effect (activity) at a higher concentration range (1-10 μM). It was also found that the IL-27 treatment suppressed the HN effect at a range of 100 nM or less (FIG. 7).

Result 11

We have developed a highly-sensitive immunofluorescence-based binding assay (2) and succeeded in detecting the association between HN and the endogenous HN receptor. This binding assay was performed using F11 cells comprising HNR at an endogenous level (FIG. 8A, left two panels), and F11 cells transfected with CNTF-R/WSX-1/gp130 so as to highly express them (right two panels). The upper two panels show the binding of HN, and the lower two panels show the binding of HNG. These results indicated that HN and HNG showed concentration-dependent binding with saturation at 10 μM and 10 nM, respectively, each KD being in a range of between 1-10 μM and 1-10 nM, respectively. The specificity of their binding was confirmed by the fact that over-addition of unlabeled HN and HNG could almost completely inhibit the binding. Binding parameters between HN or HNG and HNR that were obtained from the above results almost completely coincided with their inhibiting parameters of neuronal cell death already reported (Hashimoto et al., 2001 a, b) (FIG. 8A).

Result 12

Figure 8:
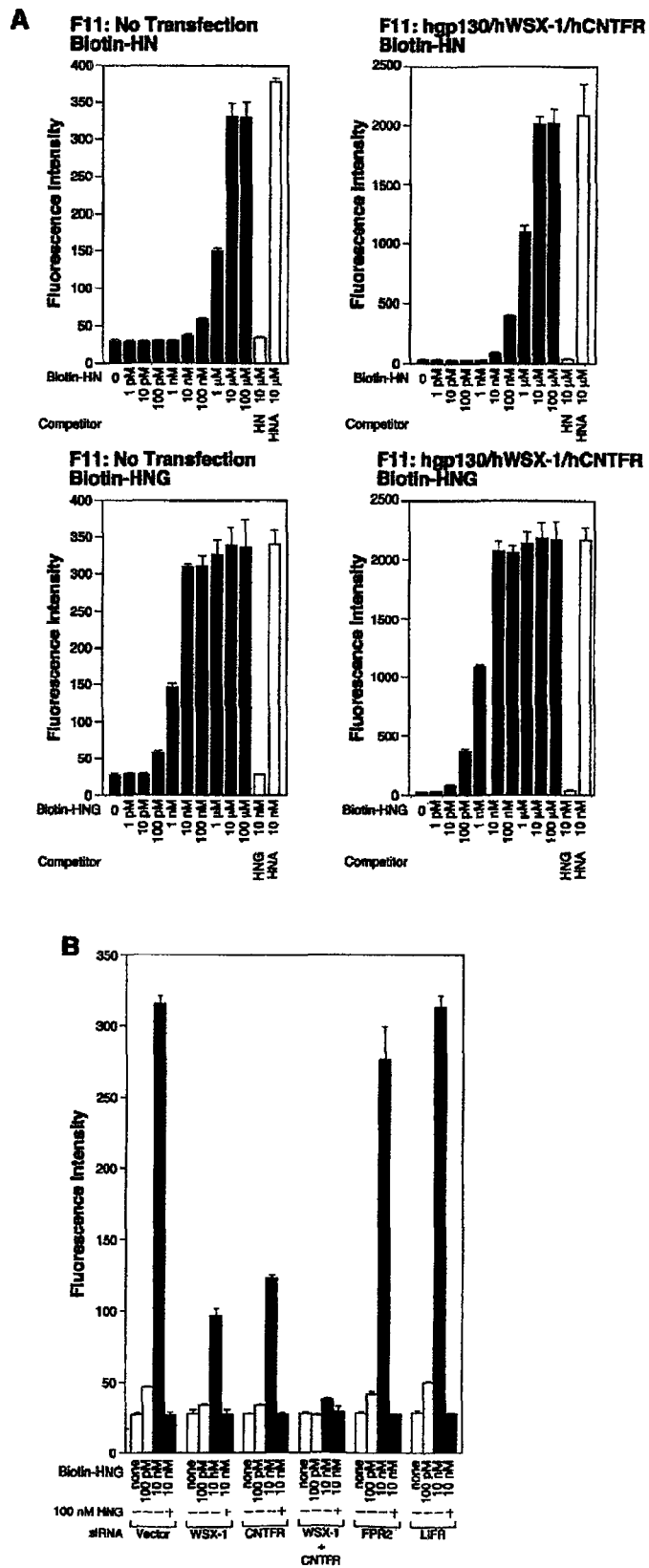

We confirmed that the binding between HN or HNG and HNR at the endogenous level would depend on the expression of CNTF-R and WSX-1 by verifying that the binding was affected by the increase of the expression of CNTF-R and WSX-1 in F11 cells by means of siRNA method (FIG. 8B). Thus, as shown in FIG. 8B, the binding was significantly decreased between HN or HNG, and F11 cells in which the expression of the endogenous CNTF-R or WSX-1 was decreased, and the above binding was almost completely inhibited in the F11 cells in which the expression of the endogenous CNTF-R and WSX-1 was simultaneously decreased. The binding was not be affected by the decrease of the expression of FPR2 or LIFR. The above results indicate that the binding between HN or HNG and F11 cells depends on the expression of CNTF-R and WSX-1.

Result 13

We further studied whether or not the treatment of PCN, a more physiological neuronal cell, with a high concentration of IL-27 and CNTF would inhibit the binding between PCN and HN in a similar manner as with F11 cells. Like the results with F11 cells, it was revealed that the IL-27 treatment in a range of 100 μM-1 μM inhibited the binding of HN to PCN (FIG. 9A). It was also observed that CNTF-R would inhibit the binding of HN to PCN in a similar range, but IL-6 did not show such effect.

Result 14

In accordance with the above binding-inhibition tests, it was shown that IL-27 had the HN-like effect at a higher concentration range while it suppressed the HN effect at a lower concentration also with respect to PCN in a similar pattern as in F1 cells (FIG. 9B). It was further observed that CNTF inhibited the HN effect like IL-27, and that the HN-effect was also inhibited by the treatment with the anti-WSX-1 antibody (mWSX-1-N). These results supported that CNTF-R/WSX-1/gp130 would function as a receptor of HN even in PCN just like in F11 cells.

Result 15

Figure 10:
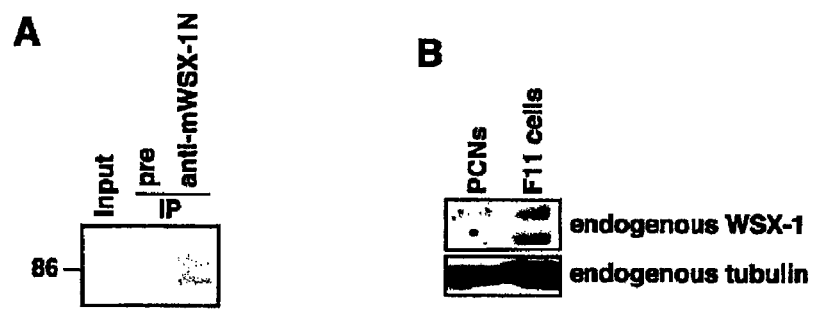

Actually, the expression of WSX-1 was confirmed also in PCN like in F11 cells (FIGS. 10A and 10B).

Result 16

Figure 11:
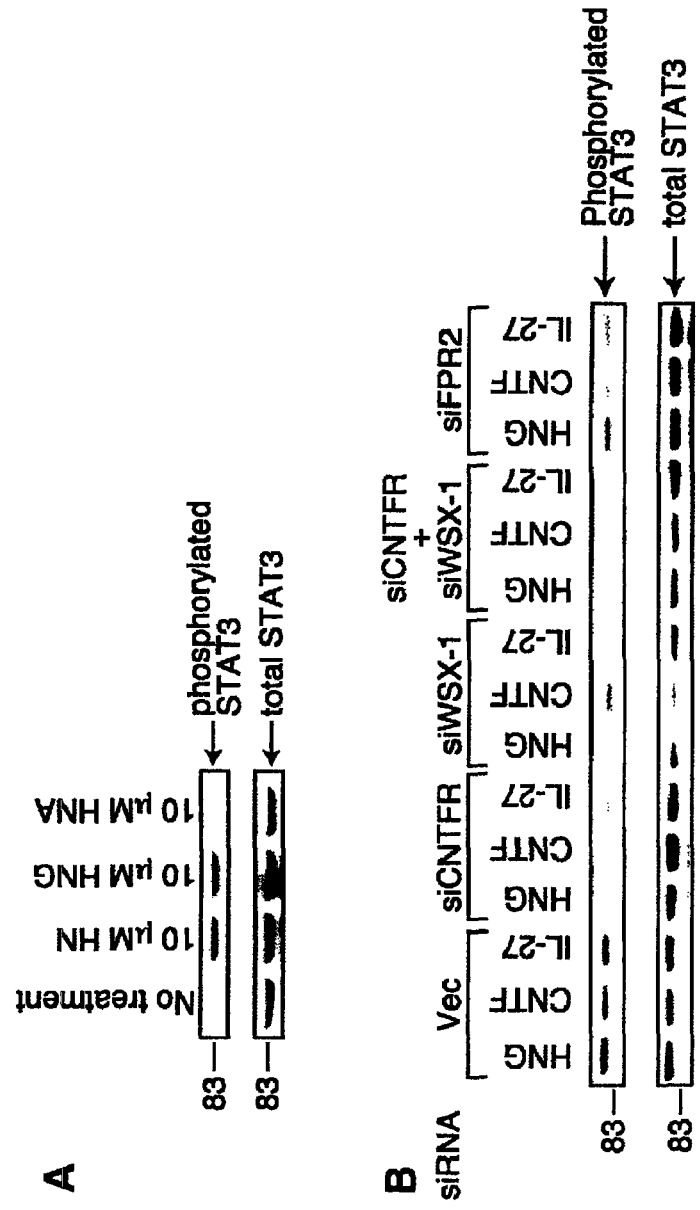

It was observed that HN and HNG increased phosphotylation of tyrosine 706 of STAT3 in F11 cells like the treatment with CNTF and IL-27 (FIG. 11A). Furthermore, the decrease of the expression of the endogenous CNTF-R or WSX-1 almost completely inhibited the phosphotylation of tyrosine 706 of STAT3 (FIG. 11B). These results indicated that HN or HNG induced phosphotylation of tyrosine 706 of STAT3 dependently on CNTF-R or WSX-1.

Result 17

Figure 12:
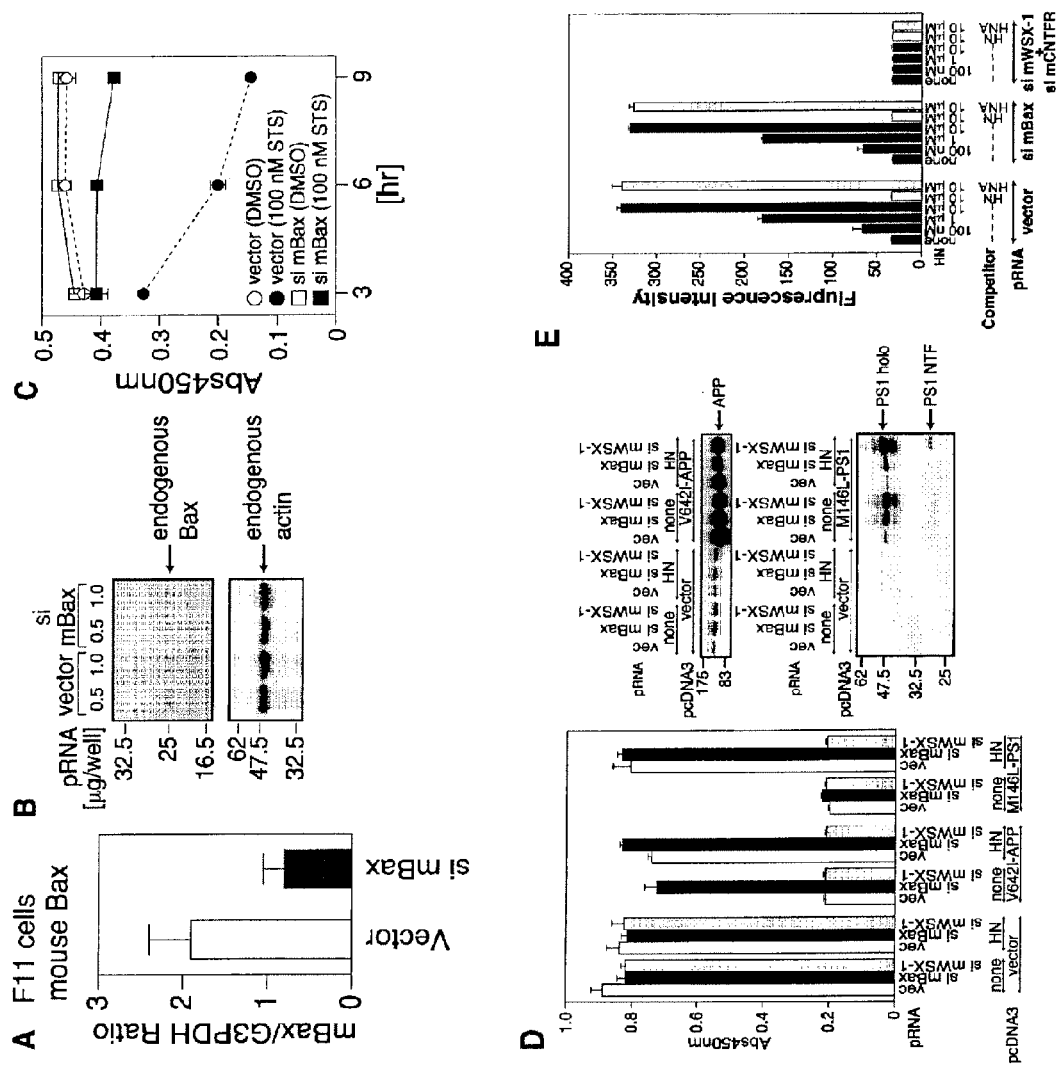

An siRNA specific to mouse Bax (siRNA-Bax) was prepared. The expression of siRNA-Bax in F11 cells significantly decreased an amount of endogenous Bax mRNA and its protein (FIGS. 12A, B). The siRNA-Bax also showed a significant inhibiting effect for apoptosis of F11 cells induced by Staurosporine (STS), leading to the conclusion that siRNA-Bax did work effectively (FIG. 12C). Then, we tested whether or not the inhibition of the expression of endogenous Bax in F11 cells by siRNA-Bax could change the inhibiting effect of HN for F11 neuronal cell death induced by a high expression of V642I-APP or M146L-PS1. The effect of siRNA for WSX-1 was first examined as a positive control. However, since it was revealed that the siRNA-Bax had the inhibiting effect for the neuronal cell death due to V642I-APP by itself, the effect of siRNA-Bax for the HN activity could not be verified in a system detecting the neuronal cell death due to V642I-APP. On the other hand, as the siRNA-Bax did not have the inhibiting effect for the neuronal cell death due to M146L-PS1, the effect of siRNA-Bax for the HN activity could be detected. As shown in FIG. 12D, the inhibition effect of HN for the neuronal cell death induced by M146L-PS1 was not affected by the inhibition of the expression of the endogenous Bax at all. It was therefore concluded that the inhibition effect of HN for the neuronal cell death did not exert via the inhibition of the function of Bax. Furthermore, FIG. 12E showed that the inhibition of the expression of the endogenous Bax did not suppress the binding activity of HN to F11 cells at all, unlike the inhibition of the expression of endogenous WSX-1 and CNTF-R. These two results showed that an intracellular Bax was not a target for HN at least in F11 cells.

The contents of the scientific journals listed below are cited and incorporated into the present specification as a part of its disclosure.

D. Artis, A. Villarino, M. Silverman, W. He, E. M. Thornton, S. Mu, S. Summer, T. M. Covey, E. Huang, H. Yoshida, G. Koretzky, M. Goldschmidt, G. D. Wu, F. de Sauvage, H. R. P. Miller, C. J. M. Saris, P. Scott, and C. A. Hunter (2004), "The IL-27 Receptor (WSX-1) is an Inhibitor of Innate and Adaptive Elements of Type 2 Immunity," J. Immunol., 173, 5626-5634.

Dimitra Benaki, Christos Zikos, Alexandra Evangelou, Evangeli Livaniou, Metaxia Vlassi, Emmanuel Mikros, and Maria Pelecanou, (2005), "Solution structure of humanin, a peptide against Alzheimer's disease-related neurotoxicity," Biochemical and Biophysical Research Communications 329, 152-160.

Jean-Louis Boulay, John J. O'Shea and William E. Paul (2003), "Molecular Phylogeny within Type I Cytokines and Their Cognate Receptors," Immunity 19, 159-163.

Martin J. Boulanger and K. Christopher Garcia (2004), "Shared Cytokine Signaling Receptors: Structural Insights from the Gp130 System," Advances in Protein Chemistry 68, 107-146.

Chen, Q., N. Ghilardi, H. Wang, T. Baker, M. H. Xie, A. Gurney, I. S. Grewal, F. J. de Sauvage, (2000), "Development of Th1-type immune responses requires type I cytokine receptor TCCR," Nature 407:916.

Dar-chone Chow, Lena Brevnova, Xiao-lin He, Monika M. Martick, Alex Bankovich and K. Christopher Garcia, (2002), "A structural template for gp130-cytokine signaling assemblies," Biochimica et Biophysica Acta (BBA)—Molecular Cell Research 1592, 225-235.

Covey, R. Faggoni, S. Mu, M. Xia, A. C. Wakeham, H. Nishina, J. Potter, et al (2001), "WSX-1 is required for the initiation of Th1 responses and resistance to L. major infection," Immunity 15:569.

Fernandez-Madrid I., Levy E., Marder K., Frangione B., 1991, "Codon 618 variant of Alzheimer amyloid gene associated with inherited cerebral hemorrhage," Annals of Neurology 30(5), 730-733.

Fukada T, Hibi M, Yamanaka Y, Takahashi-Tezuka M, Fujitani Y, Yamaguchi T, Nakajima K, Hirano T. 1996, "Two signals are necessary for cell proliferation induced by a cytokine receptor gp130: involvement of STAT3 in anti-apoptosis," Immunity 5, 449-60.

Hardy J., Selkoe D. J., 2002, "The amyloid hypothesis of Alzheimer's disease: progress and problems on the road to therapeutics," Science, 297 (5580), 353-356.

Guo, B., D. Zhai, E. Cabezas, K. Welsh, S. Nouraini, A. C. Satterthwait, and J. C. Reed 2003, "Humanin peptide suppresses apoptosis by interfering with Bax activation," Nature 423:456-461.

Hashimoto Y., Niikura T., Ito Y., Nishimoto I., 2000, "Multiple mechanisms underlie neurotoxicity by different types of Alzheimer's disease mutations of amyloid precursor protein," Journal of Biological Chemistry 275 (44), 34541-34551.

Hashimoto Y., Niikura T., Tajima H., Yasukawa T., Sudo H., Ito Y., Kita Y., Kawasumi M., Kouyama K., Doyu M., Sobue G., Koide T., Tsuji S., Lang J., Kurokawa K., Nishimoto, I., 2001a, "A rescue factor abolishing neuronal cell death by a wide spectrum of familial Alzheimer's disease genes and Aβ," Proceedings of the National Academy of Sciences of the United States of America 98 (11), 6336-6341.

Hashimoto Y., Niikura T., Ito Y., Sudo H., Hata M., Arakawa E., Abe Y., Kita Y., Nishimoto I., 2001b, "Detailed characterization of neuroprotection by a rescue factor Humanin against various Alzheimer's disease-relevant insults," Journal of Neuroscience 21 (23), 9235-9245.

Hashimoto Y., Ito Y., Arakawa E., Kita Y., Terashita K., Niikura T., Nishimoto I., 2002, "Neurotoxic mechanisms triggered by Alzheimer's disease-linked mutant M146L presenilin 1: involvement of NO synthase via a novel pertussis toxin target," Journal of Neurochemistry 80 (3), 246-237.

Hashimoto Y., Niikura T., Chiba T., Tsukamoto E., Kadowaki H., Nishitoh H., Yamagishi Y., Ishizaka M., Yamada M., Nawa M., Terashita K., Aiso S., Ichijo H., Nishimoto I., 2003, "The cytoplasmic domain of Alzheimer's amyloid precursor protein causes sustained ASK1/JNK-mediated neurotoxic signal via dimerization," Journal of Pharmacology and Experimental Therapeutics 306 (3), 889-902.

Hashimoto Y, Terashita K, Niikura T, Yamagishi Y, Ishizaka M, Kanekura K, Chiba T, Yamada M, Kita Y, Aiso S, Matsuoka M, Nishimoto I. (2004), "Humanin antagonists: mutants that interfere with dimerization inhibit neuroprotection by Humanin," Eur J Neurosci. 19:2356-64.

Hashimoto Y, Suzuki H, Aiso S, Niikura T, Nishimoto I, Matsuoka M. (2005), "Involvement of tyrosine kinases and STAT3 in Humanin-mediated neuroprotection," Life Sci. in press July 5.

Ip N Y, Yancopoulos G D. (1996), "The neurotrophins and CNTF: two families of collaborative neurotrophic factors," Annu Rev Neurosci. 1996; 19:491-515.

T. Jostock, J. Muellberg, S. oezbek, R. Atreya, G. Blinn, N. Voltz, M. Fischer, M. F. Neurath and S. Rose-John, *Eur. J. Biochem.* 268 (2001), pp. 160-167.

Jung S. S., Van Nostrand W. E., 2003, "Humanin rescues human cerebrovascular smooth muscle cells from Aβ-induced toxicity," Journal of Neurochemistry 84 (2), 266-272.

Kanekura, K., Hashimoto, Y., Niikura, T., Aiso, S., Matsuoka, M., Nishimoto, I. (2004) *J. Biol. Chem.* 279, 19247-56.

Kang J, Lemaire H G, Unterbeck A, Salbaum J M, Masters C L, Grzeschik K H, Multhaup G, Beyreuther K, Muller-Hill B (1987), "The precursor of Alzheimer's disease amyloid A4 protein resembles a cell-surface receptor," *Nature* 325: 733-736.

Kariya S., Takahashi N., Ooba N., Kawahara M., Nakayama H., Ueno S., 2002, "Humanin inhibits cell death of serum-deprived PC12 h cells," Neuroreport 13 (6), 903-907.

Kariya S., Takahashi N., Hirano M., Ueno S., 2003, "Humanin improves impaired metabolic activity and prolongs survival of serum-deprived human lymphocytes," Molecular and Cellular Biochemistry 254 (1-2), 83-89.

Kawasumi M, Chiba T, Yamada M, Miyamae-Kaneko M, Matsuoka M, Nakahara J, Tomita T, Iwatsubo T, Kato S, Aiso S, Nishimoto I, Kouyama K (2004a), "Targeted introduction of V642I mutation in amyloid precursor protein gene causes functional abnormality resembling early stage of Alzheimer's disease in aged mice," *Eur J Neurisci* 19: 2826-2838.

Kumanogoh A, Marukawa S, Kumanogoh T, Hirota H, Yoshida K, Lee I S, Yasui T, Yoshida K, Taga T, Kishimoto T. 1997, "Impairment of antigen-specific antibody production in transgenic mice expressing a dominant-negative form of gp130," Proc Natl Acad Sci USA 94, 2478-82.

Le Y., Gong W., Tiffany H. L., Tumanov A., Nedospasov S., Shen W., Dunlop N. M., Gao J.-L., Murphy P. M., Oppenheim J. J., Wang J. M., 2001, "Amyloid $\beta_{42}$ activates a G-protein-coupled chemoattractant receptor, FPR-like-1," Journal of Neuroscience 21, RC123.

Loo D. T., Copani A., Pike C. J., Whittemore E. R., Walencewicz A. J., Cotman, C. W., 1993, "Apoptosis is induced by β-amyloid in cultured central nervous system neurons," Proceedings of the National Academy of Sciences of the United States of America 90 (17), 7951-7955.

Luo J. J., Wallace W., Riccioni T., Ingram D. K., Roth G. S., Kusiak J. W., 1999, "Death of PC12 cells and hippocampal neurons induced by adenoviral-mediated FAD human amyloid precursor protein gene expression," Journal of Neuroscience Research 55 (5), 629-642.

Mueller-Newen, G., Kuester, A., Hemmann, U., Keul, R., Horsten, U., Martens, A., Graeve, L., Wijdenes, J. and Heinrich, P. C. (1998), "Soluble interleukin-6 receptor potentiates the antagonistic activity of soluble gp130 on interleukin-6 responses," J. Immunol. 161, 6347-6355.

Minami M, Inoue M, Wei S, Takeda K, Matsumoto M, Kishimoto T, Akira S. 1996, "STAT3 activation is a critical step in gp130-mediated terminal differentiation and growth arrest of a myeloid cell line," Proc Natl Acad Sci USA 93 (9):3963-6.

Monsonego A., Weiner H. L., 2003, "Immunotherapeutic Approaches to Alzheimer's Disease," Science 302 (5646), 834-838.

Neve R L, McPhie D L, Chen Y (2000), "Alzheimer's disease: a dysfunction of the amyloid precursor protein," Brain Res 886: 54-66.

Niikura T, Yamada M, Chiba T, Aiso S, Matsuoka M, Nishimoto I (2004), "Characterization of V642I-AβPP-induced cytotoxicity in primary neurons," *J Neurosci Res* 77: 54-62.

Nishimoto I, Okamoto T, Matsuura Y, Takahashi S, Okamoto T, Murayama, Y, Ogata E (1993), "Alzheimer amyloid protein precursor complexes with brain GTP binding protein Go," *Nature* 362: 75-79.

Nishimoto I., Matsuoka M., Niikura T., 2004, "Unravelling the role of Humanin," Trends in Molecular Medicine 10 (3), 102-105.

Nishimura I., Uetsuki T., Dani S. U., Ohsawa Y., Saito I., Okamura H., Uchiyama Y., Yoshikawa K., 1998, "Degeneration in vivo of rat hippocampal neurons by wild-type Alzheimer Amyloid Precursor Protein overexpressed by adenovirus-mediated gene transfer," Journal of Neuroscience 18 (7), 2387-2398.

Pelletier S., Duhamel F., Coulombe P., Popoff M. R., Meloche S., 2003, "Rho Family GTPases Are Required for Activation of Jak/STAT Signaling by G Protein-Coupled Receptors," Molecular and Cellular Biology 23 (4), 1316-1333.

Pflanz, S., J. C. Timans, J. Cheung, R. Rosales, H. Kansler, J. Gilbert, L. Hibbert, T. Churakova, M. Travis, E. Vaisberg, et al 2002, "IL-27, a heterodimeric cyokine composed of EB13 and p28 protein, induces proliferation of naive CD4+ T cells," *Immunity* 16:779.

Stefan Pflanz, Linda Hibbert, Jeanine Mattson, Rency Rosales, Elena Vaisberg, J. Fernando Bazan, Joseph H. Phillips, Terrill K. McClanahan, Rene de Waal Malefyt and Robert A. Kastelein (2004), "WSX-1 and Glycoprotein 130 Constitute a Signal-Transducing Receptor for IL-27," *The Journal of Immunology,* 172: 2225-2231.

Rawlings J. S., Rosler K. M., Harrison D. A., 2004, "The JAK/STAT signaling pathway," Journal of Cell Science 117 (Pt 8), 1281-1283.

Rohn T. T., Ivins K. J., Bahr B. A., Cotman C. W., Cribbs D. H., 2000, "A monoclonal antibody to amyloid precursor protein induces neuronal apoptosis," Journal of Cell Science 74 (6), 2331-2342.

R. Salcedo, J. K. Stauffer, E. Lincoln, T. C. Back, J. A. Hixon, C. Hahn, K. Shafer-Weaver, A. Malyguine, R. Kastelein, and J. M. Wigginton (2004), "IL-27 Mediates Complete Regression of Orthotopic Primary and Metastatic Murine Neuroblastoma Tumors: Role for CD8+ T Cells," J. Immunol. 173, 7170-7182.

Scheller J, Schuster B, Hoelscher C, Yoshimoto T, and Rose-John S. (2005), "No inhibition of IL-27 signaling by soluble gp130," Biochemical and Biophysical Research Communications 326, 724-728.

Shastry B. S., Giblin F. J., 1999, "Genes and susceptible loci of Alzheimer's disease," Brain Research Bulletin 48 (2), 121-127.

Sponne I., Fifre A., Koziel V., Kriem B., Oster T., Pillot T., 2004, "Humanin rescues cortical neurons from prion-peptide-induced apoptosis," Molecular and Cellular Neuroscience 25 (1), 95-102.

Sprecher, C. A., F. Grant, J. W. Baumgartner, S. R. Presnell, S. K. Schrader, T. Yamagiwa, T. E. Whitmore, P. J. O'Hara, D. F. Foster. 1998, "Cloning and characterization of a novel class I cytokine receptor," *Biochem. Biophys. Res. Commun.* 246: 82.

Sudo H., Hashimoto Y., Niikura T., Shao Z., Yasukawa T., Ito Y., Yamada M., Hata M., Hiraki T., Kawasumi M., Kouyama K., Nishimoto I., 2001, "Secreted Aβ does not mediate neurotoxicity by antibody-stimulated amyloid precursor protein," Biochemical Biophysical Research Communications 282 (2), 548-556.

Sui G, Soohoo C, Affar E B, Gay F, Shi Y, Forrester W C, Shi Y (2002), "A DNA vector-based RNAi technology to suppress gene expression in mammalian cells," *Proc Natl Acad Sci USA* 99: 5515-5520.

Tajima H, Kawasumi M, Chiba T, Yamada M, Yamashita K, Nawa M, Kita Y, Kouyama K, Aiso S, Matsuoka M, Niikura T, Nishimoto I. (2005), "A humanin derivative, S14 G-HN, prevents amyloid-beta-induced memory impairment in mice," J Neurosci Res. 2005 79, 714-23.

Terashita K., Hashimoto Y., Niikura T., Tajima H., Yamagishi Y., Ishizaka M.,

Kawasumi M., Chiba T., Kanekura K., Yamada M., Nawa M., Kita Y., Aiso S., Nishimoto I., 2003, "Two Ser residues distinctly regulate the rescue function of Humanin, an inhibiting factor of Alzheimer's disease-related neurotoxicity: functional potentiation by isomerization and dimerization," Journal of Neurochemistry 85 (6), 1521-1538.

Tetsuya Taga (1997), "gp130 AND THE INTERLEUKIN-6 FAMILY OF CYTOKINES," Annual Review of Immunology 15: 797-819.

Tsukamoto E., Hashimoto Y., Kanekura K., Niikura T., Aiso S., Nishimoto I., 2003, "Characterization of the toxic mechanism triggered by Alzheimer's amyloid-β peptides via p75 neurotrophin receptor in neuronal hybrid cells," Journal of Neuroscience Research 73 (5), 627-636.

Turkson J., Jove R. 2000, "STAT proteins: novel molecular targets for cancer drug discovery," Oncogene 19 (56), 6613-6626.

Wolozin B., Iwasaki K., Vito P., Ganjei J. K., Lacana E., Sunderland T., Zhao B., Kusiak J. W., Wasco W., D'Adamio L., 1996, "Participation of presenilin 2 in apoptosis: enhanced basal activity conferred by an Alzheimer mutation," Science 274 (5293), 1710-1713.

Yamagishi Y, Hashimoto Y, Niikura T, Nishimoto I. (2003), "Identification of essential amino acids in Humanin, a neuroprotective factor against Alzheimer's disease-relevant insults," Peptides 24, 585-95.

Yamatsuji T., Matsui T., Okamoto T., Komatsuzaki K., Takeda S., Fukumoto H., Iwatsubo T., Suzuki N., Asami-Odaka A., Ireland S., Kinane T. B., Giambarella U., Nishimoto I., 1996a, "G protein-mediated neuronal DNA fragmentation induced by familial Alzheimer's disease-associated mutants of APP," Science 272 (5226), 1349-1352.

Yamatsuji T., Okamoto T., Takeda S., Murayama Y., Tanaka N., Nishimoto I., 1996b, "Expression of V642 APP mutant causes cellular apoptosis as Alzheimer trait-linked phenotype," EMBO Journal 15 (3), 498-509.

Ying G., Iribarren P., Zhou Y., Gong W., Zhang N., Yu Z. X., Le Y., Cui Y., Wang J. M., 2004, "Humanin, a newly identified neuroprotective factor, uses the G protein-coupled formylpeptide receptor-like-1 as a functional receptor," Journal of Immunology 172 (11), 7078-7085.

Yoshida, H., S. Hamano, G. Senaldi, T. A. V. Villarino, E. Huang, and C. A. Hunter (2004), "Understanding the Pro- and Anti-Inflammatory Properties of IL-27," J. Immunol., 173, 715-720.

WO01/021787, Polypeptide inhibiting neuronal cell death, Humanin.

WO03/097687, Neuroprotective Polypeptide and Methods of Use.

WO00/14204, Nerve Cell Death Receptor.

INDUSTRIAL APPLICABILITY

Humanin-like polypeptide receptor (HNR) revealed by the present invention is useful in revealing a mechanism of promoting or suppressing the intracellular signal transduction for showing neuroprotecting activity of HN, and is utilized in a clinical application of development of a drug for the treatment of neurodegenerative disease, especially Alzheimer's disease.

What is claimed is:

1. An isolated Humanin receptor consisting of three polypeptides:
   (i) gp130 or a partial polypeptide of gp130;
   (ii) CNTF-R; and
   (iii) WSX-1,
   wherein the partial polypeptide of gp130 comprises at least amino acid residues 1-133 (SEQ ID NO:37) of the intracellular domain of gp130.

2. The Humanin receptor of claim 1, wherein the three polypeptides are derived from human.

* * * * *

SEQUENCE LISTING

```
<160> NUMBER OF SEQ ID NOS: 39

<210> SEQ ID NO 1
<211> LENGTH: 24
<212> TYPE: PRT
<213> ORGANISM: Homo sapiens

<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 2
<211> LENGTH: 10
<212> TYPE: PRT
<213> ORGANISM: Artificial Sequence
<220> FEATURE:
<223> OTHER INFORMATION: synthetic sequence
```

```
<220> FEATURE:
<221> NAME/KEY: MISC_FEATURE
<222> LOCATION: (2)..(5)
<223> OTHER INFORMATION: The Xaa at positions 2 and 5 is any amino acid
      sequence of ten or fewer amino acids
      The Xaa at position 3 is Cys or a basic amino acid
      The Xaa at position 4 is Leu or Arg
<220> FEATURE:
<221> NAME/KEY: MISC_FEATURE
<222> LOCATION: (8)..(9)
<223> OTHER INFORMATION: The Xaa at position 8 is Gly or Ser
      The Xaa at position 9 is any amino acid sequence of ten or fewer
      amino acids

<400> SEQUENCE: 2

Pro Xaa Xaa Xaa Xaa Leu Thr Xaa Xaa Pro
1               5                   10

<210> SEQ ID NO 3
<211> LENGTH: 26
<212> TYPE: DNA
<213> ORGANISM: artificial sequence
<220> FEATURE:
<223> OTHER INFORMATION: PCR primer

<400> SEQUENCE: 3
actagtacca tgcggggagg cagggg                                         26

<210> SEQ ID NO 4
<211> LENGTH: 26
<212> TYPE: DNA
<213> ORGANISM: Artificial Sequence
<220> FEATURE:
<223> OTHER INFORMATION: PCR primer

<400> SEQUENCE: 4
gaattcggcc agaacctgtg gcctgg                                         26

<210> SEQ ID NO 5
<211> LENGTH: 29
<212> TYPE: DNA
<213> ORGANISM: Artificial Sequence
<220> FEATURE:
<223> OTHER INFORMATION: PCR primer

<400> SEQUENCE: 5
ggatccacca tgaagggcgc gatggagcc                                      29

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
gaattcaaat accagcactt tccatccagg                                     30

<210> SEQ ID NO 7
<211> LENGTH: 16
<212> TYPE: PRT
<213> ORGANISM: Artificial Sequence
<220> FEATURE:
<223> OTHER INFORMATION: synthetic peptide

<400> SEQUENCE: 7

Met Asn Arg Leu Arg Val Ala Arg Leu Thr Pro Leu Glu Leu Leu Leu
1               5                   10                  15
```

```
<210> SEQ ID NO 8
<211> LENGTH: 19
<212> TYPE: PRT
<213> ORGANISM: Artificial Sequence
<220> FEATURE:
<223> OTHER INFORMATION: synthetic peptide

<400> SEQUENCE: 8

Tyr Ser Gly Tyr Glu Lys His Phe Leu Pro Thr Pro Glu Glu Leu Gly
1               5                   10                  15

Leu Leu Val

<210> SEQ ID NO 9
<211> LENGTH: 17
<212> TYPE: PRT
<213> ORGANISM: Artificial Sequence
<220> FEATURE:
<223> OTHER INFORMATION: synthetic peptide

<400> SEQUENCE: 9

Met Arg Gly Gly Arg Gly Ala Pro Phe Trp Leu Trp Pro Leu Pro Lys
1               5                   10                  15

Cys

<210> SEQ ID NO 10
<211> LENGTH: 20
<212> TYPE: PRT
<213> ORGANISM: Artificial Sequence
<220> FEATURE:
<223> OTHER INFORMATION: synthetic peptide

<400> SEQUENCE: 10

Leu Pro Thr Pro Glu Glu Leu Gly Leu Leu Gly Pro Pro Arg Pro Gln
1               5                   10                  15

Val Leu Ala Cys
            20

<210> SEQ ID NO 11
<211> LENGTH: 80
<212> TYPE: DNA
<213> ORGANISM: Artificial Sequence
<220> FEATURE:
<223> OTHER INFORMATION: DNA fragment

<400> SEQUENCE: 11
aggatcccgt aactaccact aagcaatgtc ttgatatccg gacattgctt agtggtagtt      60 atttttttcca aaagcttgca                                                 80

<210> SEQ ID NO 12
<211> LENGTH: 80
<212> TYPE: DNA
<213> ORGANISM: Artificial Sequence
<220> FEATURE:
<223> OTHER INFORMATION: DNA fragment

<400> SEQUENCE: 12
tgcaagcttt tggaaaaaat aactaccact aagcaatgtc cggatatcaa gacattgctt      60
agtggtagtt acgggatcct                                                  80

<210> SEQ ID NO 13
<211> LENGTH: 80
<212> TYPE: DNA
<213> ORGANISM: Artificial Sequence
<220> FEATURE:
```

<223> OTHER INFORMATION: DNA fragment

<400> SEQUENCE: 13
ttggatcccg tgtgtgctgt gccatccgag attgatatcc gtctcggatg gcacagcaca       60
cattttttcc aaggtacctt                                                   80

<210> SEQ ID NO 14
<211> LENGTH: 78
<212> TYPE: DNA
<213> ORGANISM: Artificial Sequence
<220> FEATURE:
<223> OTHER INFORMATION: DNA fragment

<400> SEQUENCE: 14
aaggtacctt ggaaaaaatg tgtgctgtgc catccgagac ggatatcaat ctcggatggc       60
acagcacacg ggatccaa                                                     78

<210> SEQ ID NO 15
<211> LENGTH: 78
<212> TYPE: DNA
<213> ORGANISM: Artificial Sequence
<220> FEATURE:
<223> OTHER INFORMATION: DNA fragment

<400> SEQUENCE: 15
ttggatccca tatccacttg agagaagatc ttgatatccg gatcttctct caagggatat       60
ttttttccaa ggtacctt                                                     78

<210> SEQ ID NO 16
<211> LENGTH: 78
<212> TYPE: DNA
<213> ORGANISM: Artificial Sequence
<220> FEATURE:
<223> OTHER INFORMATION: DNA fragment

<400> SEQUENCE: 16
aaggtacctt ggaaaaaaat atccacttga ggaagatccg gatatcaaga tcttctctca       60
agtggatatg ggatccaa                                                     78

<210> SEQ ID NO 17
<211> LENGTH: 80
<212> TYPE: DNA
<213> ORGANISM: Artificial Sequence
<220> FEATURE:
<223> OTHER INFORMATION: DNA fragment

<400> SEQUENCE: 17
gcggatcccg tttaagctgt gaaacgcttc gttgatatcc gcgaagcgtt tcacagctta       60
aattttttcc aaaagcttgc                                                   80

<210> SEQ ID NO 18
<211> LENGTH: 80
<212> TYPE: DNA
<213> ORGANISM: Artificial Sequence
<220> FEATURE:
<223> OTHER INFORMATION: DNA fragment

<400> SEQUENCE: 18
gcaagctttt ggaaaaaatt taagctgtga aacgcttcgc ggatatcaac gaagcgtttc       60
acagcttaaa cgggatccgc                                                   80

<210> SEQ ID NO 19

```
<211> LENGTH: 78
<212> TYPE: DNA
<213> ORGANISM: Artificial Sequence
<220> FEATURE:
<223> OTHER INFORMATION: DNA fragment

<400> SEQUENCE: 19
ttggatccca tatccacttg agagaagatc ttgatatccg gatcttctct caagggatat    60 tttttttccaa ggtaccttt                                                78

<210> SEQ ID NO 20
<211> LENGTH: 78
<212> TYPE: DNA
<213> ORGANISM: Artificial Sequence
<220> FEATURE:
<223> OTHER INFORMATION: DNA fragment

<400> SEQUENCE: 20
aaggtacctt ggaaaaaaat atccacttga ggaagatccg gatatcaaga tcttctctca    60
agtggatatg ggatccaa                                                  78

<210> SEQ ID NO 21
<211> LENGTH: 79
<212> TYPE: DNA
<213> ORGANISM: Artificial Sequence
<220> FEATURE:
<223> OTHER INFORMATION: DNA fragment

<400> SEQUENCE: 21
cgggatccca tgatctgttc agagctggtg ttgatatccg caccagctct gaacagatca    60 ttttttttcca aggtacccc                                                79

<210> SEQ ID NO 22
<211> LENGTH: 79
<212> TYPE: DNA
<213> ORGANISM: Artificial Sequence
<220> FEATURE:
<223> OTHER INFORMATION: DNA fragment

<400> SEQUENCE: 22
ggggtacctt ggaaaaaaat gatctgttca gagctggtgc ggatatcaac accagctctg    60
aacagatcat gggatcccg                                                 79

<210> SEQ ID NO 23
<211> LENGTH: 23
<212> TYPE: DNA
<213> ORGANISM: Artificial Sequence
<220> FEATURE:
<223> OTHER INFORMATION: PCR primer

<400> SEQUENCE: 23
ttccaccgtg actcctgcac ctg                                            23

<210> SEQ ID NO 24
<211> LENGTH: 24
<212> TYPE: DNA
<213> ORGANISM: Artificial Sequence
<220> FEATURE:
<223> OTHER INFORMATION: PCR primer

<400> SEQUENCE: 24
gagggctggg tccttctcac agac                                           24

<210> SEQ ID NO 25
```

```
<211> LENGTH: 24
<212> TYPE: DNA
<213> ORGANISM: Artificial Sequence
<220> FEATURE:
<223> OTHER INFORMATION: PCR primer

<400> SEQUENCE: 25
ccgcagaaag ctctcacctg tcag                                           24

<210> SEQ ID NO 26
<211> LENGTH: 24
<212> TYPE: DNA
<213> ORGANISM: Artificial Sequence
<220> FEATURE:
<223> OTHER INFORMATION: PCR primer

<400> SEQUENCE: 26
ccatggatat ccgttctcca cctg                                           24

<210> SEQ ID NO 27
<211> LENGTH: 24
<212> TYPE: DNA
<213> ORGANISM: Artificial Sequence
<220> FEATURE:
<223> OTHER INFORMATION: PCR primer

<400> SEQUENCE: 27
gtggaagata cgtcggcaga ctcg                                           24

<210> SEQ ID NO 28
<211> LENGTH: 24
<212> TYPE: DNA
<213> ORGANISM: Artificial Sequence
<220> FEATURE:
<223> OTHER INFORMATION: PCR primer

<400> SEQUENCE: 28
accctgaagg tcagcaatcc tcag                                           24

<210> SEQ ID NO 29
<211> LENGTH: 24
<212> TYPE: DNA
<213> ORGANISM: Artificial Sequence
<220> FEATURE:
<223> OTHER INFORMATION: PCR primer

<400> SEQUENCE: 29
ccctgccagt attctcagca gctg                                           24

<210> SEQ ID NO 30
<211> LENGTH: 24
<212> TYPE: DNA
<213> ORGANISM: Artificial Sequence
<220> FEATURE:
<223> OTHER INFORMATION: PCR primer

<400> SEQUENCE: 30
cggccttcca ggtatggctg atac                                           24

<210> SEQ ID NO 31
<211> LENGTH: 31
<212> TYPE: DNA
<213> ORGANISM: Artificial Sequence
<220> FEATURE:
<223> OTHER INFORMATION: PCR primer

<400> SEQUENCE: 31
```

```
ggaattcacc atggacgggt ccggggagca g                                    31
```

<210> SEQ ID NO 32
<211> LENGTH: 32
<212> TYPE: DNA
<213> ORGANISM: Artificial Sequence
<220> FEATURE:
<223> OTHER INFORMATION: PCR primer

<400> SEQUENCE: 32

```
ggggtaccgc ccatcttctt ccagatggtg ag                                   32
```

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33

```
tccaccaccc tgttgctgta                                                 20
```

<210> SEQ ID NO 34
<211> LENGTH: 20
<212> TYPE: DNA
<213> ORGANISM: Artificial Sequence
<220> FEATURE:
<223> OTHER INFORMATION: PCR primer

<400> SEQUENCE: 34

```
accacagtcc atgccatcac                                                 20
```

<210> SEQ ID NO 35
<211> LENGTH: 277
<212> TYPE: PRT
<213> ORGANISM: Homo sapiens

<400> SEQUENCE: 35

```
Asn Lys Arg Asp Leu Ile Lys Lys His Ile Trp Pro Asn Val Pro Asp
1               5                   10                  15

Pro Ser Lys Ser His Ile Ala Gln Trp Ser Pro His Thr Pro Pro Arg
            20                  25                  30

His Asn Phe Asn Ser Lys Asp Gln Met Tyr Ser Asp Gly Asn Phe Thr
        35                  40                  45

Asp Val Ser Val Val Glu Ile Glu Ala Asn Asp Lys Lys Pro Phe Pro
    50                  55                  60

Glu Asp Leu Lys Ser Leu Asp Leu Phe Lys Lys Gly Lys Ile Asn Thr
65                  70                  75                  80

Glu Gly His Ser Ser Gly Ile Gly Gly Ser Ser Cys Met Ser Ser Ser
                85                  90                  95

Arg Pro Ser Ile Ser Ser Asp Glu Asn Glu Ser Ser Gln Asn Thr
            100                 105                 110

Ser Ser Thr Val Gln Tyr Ser Thr Val Val His Ser Gly Tyr Arg His
        115                 120                 125

Gln Val Pro Ser Val Gln Val Phe Ser Arg Ser Glu Ser Thr Gln Pro
    130                 135                 140

Leu Leu Asp Ser Glu Glu Arg Pro Glu Asp Leu Gln Leu Val Asp His
145                 150                 155                 160

Val Asp Gly Gly Asp Gly Ile Leu Pro Arg Gln Gln Tyr Phe Lys Gln
                165                 170                 175

Asn Cys Ser Gln His Glu Ser Ser Pro Asp Ile Ser His Phe Glu Arg
```

-continued

```
                180                 185                 190
Ser Lys Gln Val Ser Val Asn Glu Glu Asp Phe Val Arg Leu Lys
        195                 200                 205

Gln Gln Ile Ser Asp His Ile Ser Gln Ser Cys Gly Ser Gly Gln Met
    210                 215                 220

Lys Met Phe Gln Glu Val Ser Ala Ala Asp Ala Phe Gly Pro Gly Thr
225                 230                 235                 240

Glu Gly Gln Val Glu Arg Phe Glu Thr Val Gly Met Glu Ala Ala Thr
                245                 250                 255

Asp Glu Gly Met Pro Lys Ser Tyr Leu Pro Gln Thr Val Arg Gln Gly
                260                 265                 270

Gly Tyr Met Pro Gln
        275

<210> SEQ ID NO 36
<211> LENGTH: 195
<212> TYPE: PRT
<213> ORGANISM: Homo sapiens

<400> SEQUENCE: 36

Asn Lys Arg Asp Leu Ile Lys Lys His Ile Trp Pro Asn Val Pro Asp
1               5                   10                  15

Pro Ser Lys Ser His Ile Ala Gln Trp Ser Pro His Thr Pro Pro Arg
            20                  25                  30

His Asn Phe Asn Ser Lys Asp Gln Met Tyr Ser Asp Gly Asn Phe Thr
        35                  40                  45

Asp Val Ser Val Val Glu Ile Glu Ala Asn Asp Lys Lys Pro Phe Pro
    50                  55                  60

Glu Asp Leu Lys Ser Leu Asp Leu Phe Lys Lys Glu Lys Ile Asn Thr
65                  70                  75                  80

Glu Gly His Ser Ser Gly Ile Gly Gly Ser Ser Cys Met Ser Ser Ser
                85                  90                  95

Arg Pro Ser Ile Ser Ser Ser Asp Glu Asn Glu Ser Ser Gln Asn Thr
            100                 105                 110

Ser Ser Thr Val Gln Tyr Ser Thr Val Val His Ser Gly Tyr Arg His
        115                 120                 125

Gln Val Pro Ser Val Gln Val Phe Ser Arg Ser Glu Ser Thr Gln Pro
    130                 135                 140

Leu Leu Asp Ser Glu Glu Arg Pro Glu Asp Leu Gln Leu Val Asp His
145                 150                 155                 160

Val Asp Gly Gly Asp Gly Ile Leu Pro Arg Gln Gln Tyr Phe Lys Gln
                165                 170                 175

Asn Cys Ser Gln His Glu Ser Ser Pro Asp Ile Ser His Phe Glu Arg
            180                 185                 190

Ser Lys Gln
        195

<210> SEQ ID NO 37
<211> LENGTH: 133
<212> TYPE: PRT
<213> ORGANISM: Homo sapiens

<400> SEQUENCE: 37

Asn Lys Arg Asp Leu Ile Lys Lys His Ile Trp Pro Asn Val Pro Asp
1               5                   10                  15

Pro Ser Lys Ser His Ile Ala Gln Trp Ser Pro His Thr Pro Pro Arg
            20                  25                  30
```

```
His Asn Phe Asn Ser Lys Asp Gln Met Tyr Ser Asp Gly Asn Phe Thr
            35                  40                  45

Asp Val Ser Val Val Glu Ile Glu Ala Asn Asp Lys Lys Pro Phe Pro
    50                  55                  60

Glu Asp Leu Lys Ser Leu Asp Leu Phe Lys Lys Glu Lys Ile Asn Thr
65                  70                  75                  80

Glu Gly His Ser Ser Gly Ile Gly Gly Ser Ser Cys Met Ser Ser Ser
                85                  90                  95

Arg Pro Ser Ile Ser Ser Ser Asp Glu Asn Glu Ser Ser Gln Asn Thr
                100                 105                 110

Ser Ser Thr Val Gln Tyr Ser Thr Val Val His Ser Gly Tyr Arg His
            115                 120                 125

Gln Val Pro Ser Val
        130

<210> SEQ ID NO 38
<211> LENGTH: 68
<212> TYPE: PRT
<213> ORGANISM: Homo sapiens

<400> SEQUENCE: 38

Asn Lys Arg Asp Leu Ile Lys Lys His Ile Trp Pro Asn Val Pro Asp
1               5                   10                  15

Pro Ser Lys Ser His Ile Ala Gln Trp Ser Pro His Thr Pro Pro Arg
            20                  25                  30

His Asn Phe Asn Ser Lys Asp Gln Met Tyr Ser Asp Gly Asn Phe Thr
            35                  40                  45

Asp Val Ser Val Val Glu Ile Glu Ala Asn Asp Lys Lys Pro Phe Pro
    50                  55                  60

Glu Asp Leu Lys
65

<210> SEQ ID NO 39
<211> LENGTH: 25
<212> TYPE: PRT
<213> ORGANISM: Homo sapiens

<400> SEQUENCE: 39

Asn Lys Arg Asp Leu Ile Lys Lys His Ile Trp Pro Asn Val Pro Asp
1               5                   10                  15

Pro Ser Lys Ser His Ile Ala Gln Trp
            20                  25
```